(12) United States Patent
Abrahamsson

(10) Patent No.: US 11,783,928 B2
(45) Date of Patent: Oct. 10, 2023

(54) MEDICAL DATA COLLECTION DEVICES, SYSTEMS, AND METHODS

(71) Applicant: GAMBRO LUNDIA AB, Lund (SE)

(72) Inventor: Anders Abrahamsson, Sodra Sandby (SE)

(73) Assignee: Gambro Lundia AB, Lund (SE)

( * ) Notice: Subject to any disclaimer, the term of this patent is extended or adjusted under 35 U.S.C. 154(b) by 104 days.

(21) Appl. No.: 16/967,357

(22) PCT Filed: Feb. 4, 2019

(86) PCT No.: PCT/EP2019/052583
§ 371 (c)(1),
(2) Date: Aug. 4, 2020

(87) PCT Pub. No.: WO2019/154744
PCT Pub. Date: Aug. 15, 2019

(65) Prior Publication Data
US 2021/0035670 A1     Feb. 4, 2021

(30) Foreign Application Priority Data
Feb. 9, 2018    (SE) .................................. 1850143-7

(51) Int. Cl.
    *G16H 10/60*       (2018.01)
    *G16H 15/00*       (2018.01)
             (Continued)

(52) U.S. Cl.
CPC ............. *G16H 15/00* (2018.01); *G16H 10/60* (2018.01); *G16H 30/00* (2018.01); *G16H 40/20* (2018.01);
(Continued)

(58) Field of Classification Search
CPC ........ G16H 15/00; G16H 10/60; G16H 30/00; G16H 40/20; G16H 80/00; G06K 7/1417; G06V 20/20
See application file for complete search history.

(56) References Cited

U.S. PATENT DOCUMENTS

| 2009/0192813 A1 | 7/2009 | Gejdos | |
| 2011/0010257 A1* | 1/2011 | Hill | ...................... G06Q 10/087 |
| | | | 705/28 |

(Continued)

OTHER PUBLICATIONS

Android Labs: Bluetooth HID device implementation (your phone as a mouse+voice control) (https://hsc.com/Blog/Android-Labs-Bluetooth-HID-device implementaion-your-phone-as-a-mouse-voice-control); Jan. 28, 2015—24 pages.

(Continued)

*Primary Examiner* — Jonathan Ng
*Assistant Examiner* — Benjamin L. Hanks
(74) *Attorney, Agent, or Firm* — K&L Gates LLP

(57) ABSTRACT

A system, method, and device for medical data collection are disclosed. An example portable device includes a camera configured to record images, a memory storing the recorded images, and a display interface for displaying the images. The portable device also includes a processor configured to instruct the camera to record at least one of the images and extract medical data from the at least one image using an optical character recognition routine. The example processor is further configured to establish a connection with a clinician computer such that the portable device is recognized by the clinician computer as a keyboard. Moreover, the example processor is configured to transmit at least some of the extracted medical data to the clinician computer as a keyboard input to the clinician computer.

28 Claims, 17 Drawing Sheets

(51) Int. Cl.
　　*G16H 40/20*　　(2018.01)
　　*G16H 30/00*　　(2018.01)
　　*G16H 80/00*　　(2018.01)
　　*G06K 7/14*　　(2006.01)
　　*G06V 20/20*　　(2022.01)
(52) U.S. Cl.
　　CPC ........... *G16H 80/00* (2018.01); *G06K 7/1417* (2013.01); *G06V 20/20* (2022.01)

(56) References Cited

U.S. PATENT DOCUMENTS

| | | |
|---|---|---|
| 2011/0309955 A1 | 12/2011 | Ahmadi |
| 2013/0129217 A1 | 5/2013 | Gupta |
| 2014/0009473 A1 | 1/2014 | Korkishko |
| 2014/0098209 A1 | 4/2014 | Neff |
| 2014/0320677 A1 | 10/2014 | Jarvenpaa et al. |
| 2015/0182114 A1* | 7/2015 | Wang ..................... A61B 90/90 600/549 |
| 2016/0299001 A1* | 10/2016 | Petrucelli ............. A61B 5/0537 |
| 2017/0220769 A1* | 8/2017 | Miller .................... G16H 40/63 |
| 2018/0040123 A1* | 2/2018 | Neff ...................... G06T 7/0012 |
| 2019/0392929 A1* | 12/2019 | Gassman ............... G16H 40/63 |

OTHER PUBLICATIONS

International Search Report for PCT/EP2019/052583 dated May 27, 2019—4 pages.

Written Opinion for PCT/EP2019/052583 dated May 27, 2019—8 pages.

* cited by examiner

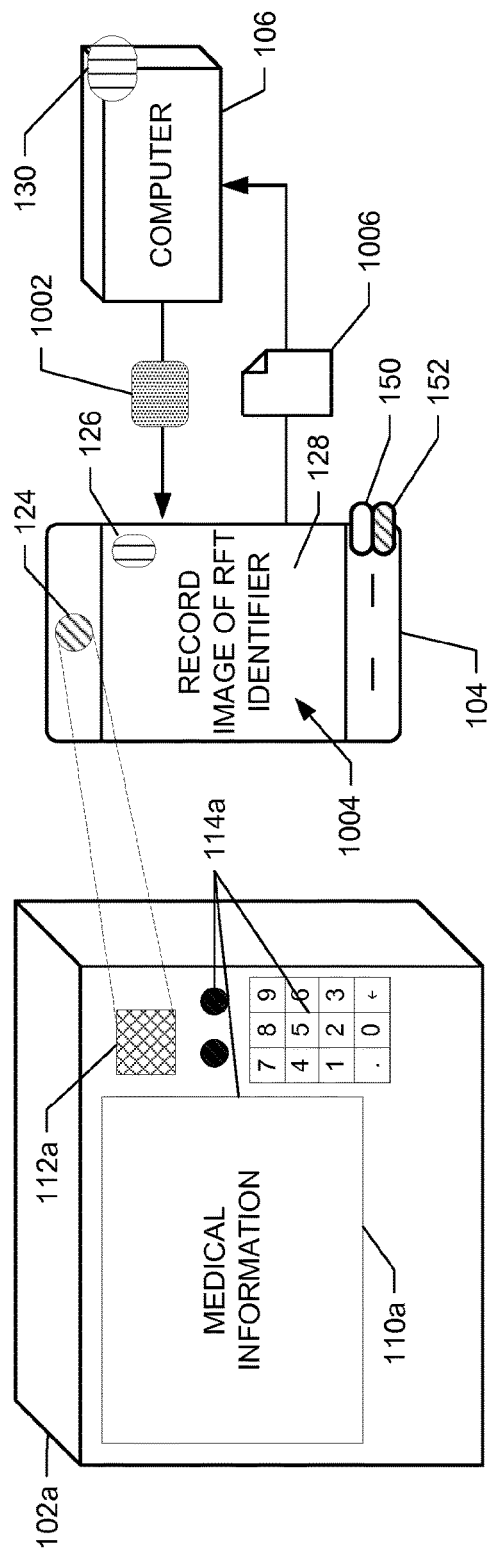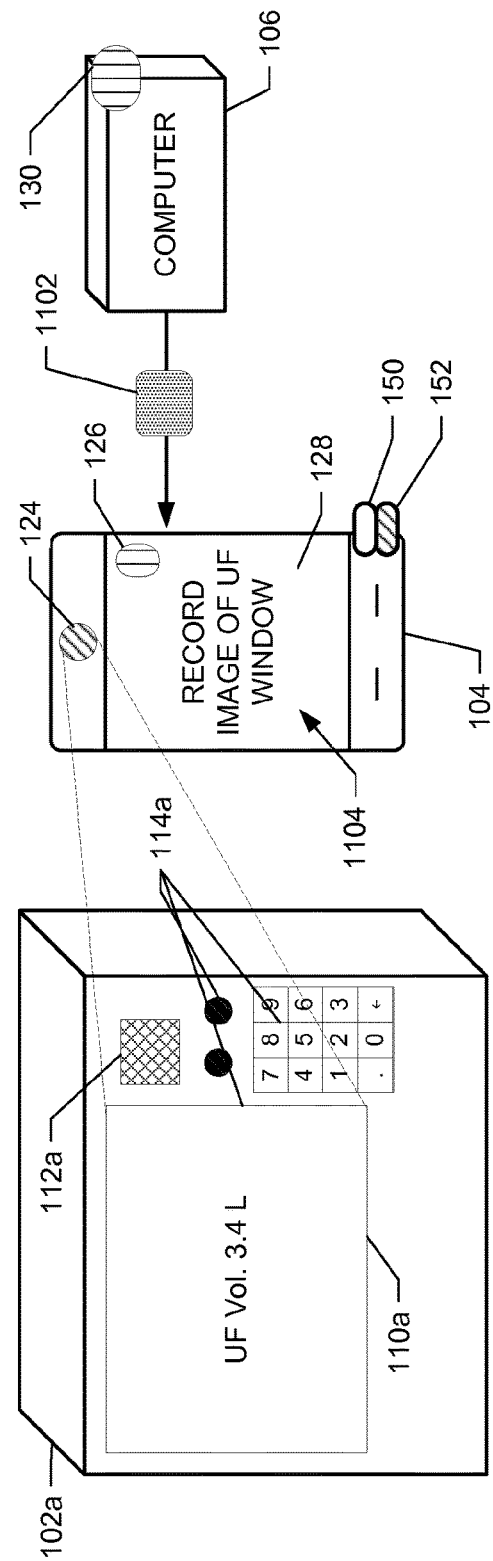

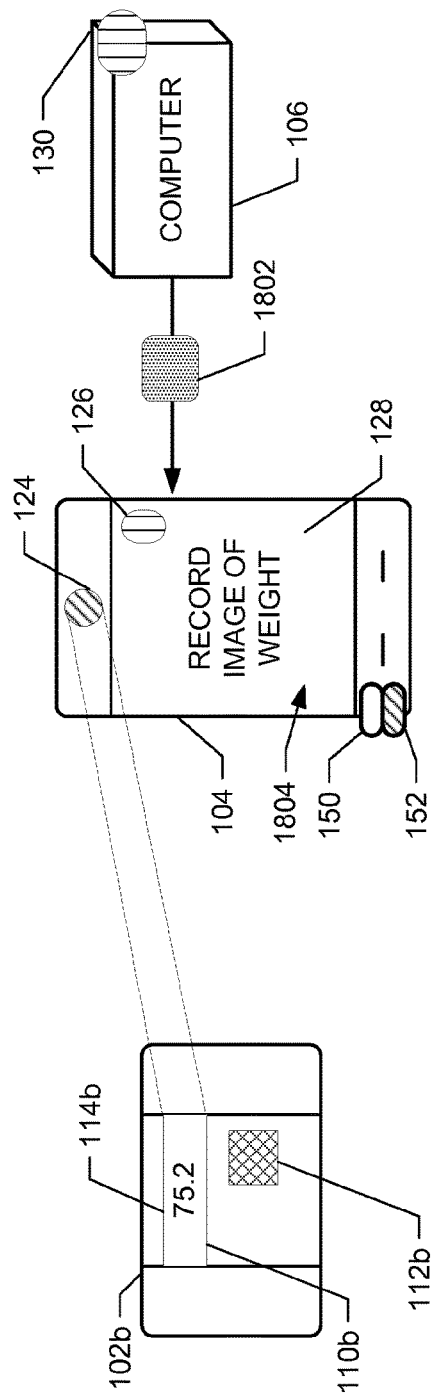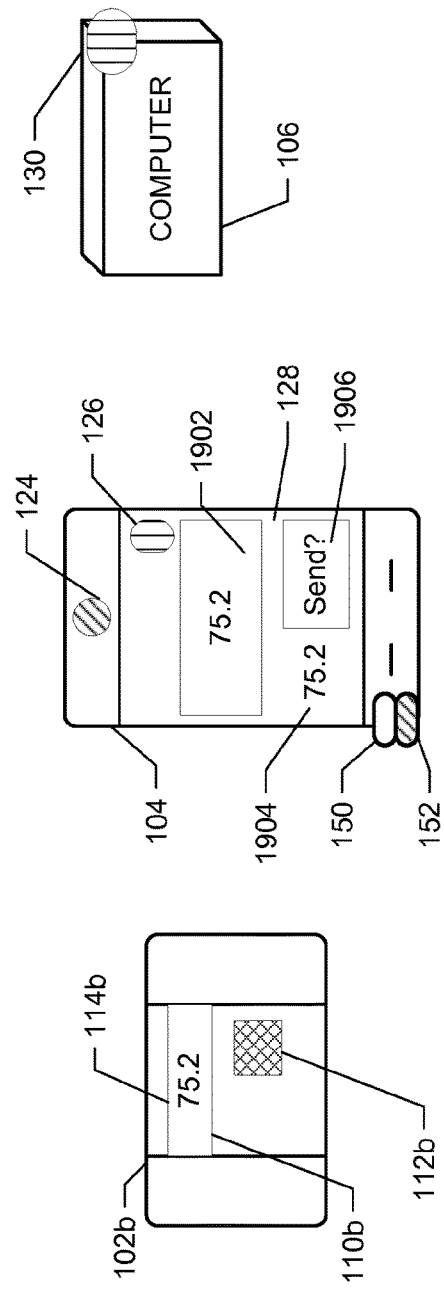

MEDICAL DATA COLLECTION DEVICES, SYSTEMS, AND METHODS

PRIORITY CLAIM

This application is a national phase entry of PCT/EP2019/052583, filed Feb. 4, 2019, which claims priority to Swedish Patent Application No. 1850143-7, filed Feb. 9, 2018, the entire disclosures of which are incorporated by reference herein.

TECHNICAL FIELD

The present disclosure relates generally to methods and apparatuses for collecting medical information. In particular, the present disclosure relates to a portable device that transmits medical information extracted from images to a clinician computer as a keyboard input.

BACKGROUND

Oftentimes network connectivity is taken for granted in developed regions of the world. People generally assume a Wi-Fi or cellular network is available for sending and receiving data, media content, email, etc. Even in medical environments, people expect that network connectivity exists to enable most devices to community with each other. While this may be true of advanced medical centers, many others, such as clinics, dialysis centers, and rural care centers do not have the luxury of device interconnectivity. Further, many rural treatment centers and clinics in developing regions operate with limited supplies and medical devices, many of which are relatively low cost and do not have connection capability or are not compatible with each other.

Generally, device connectivity enables the automatic documentation of medical device data, such as patient treatment data and measured patient physiological data. For example, a blood pressure monitor may wirelessly pair with a renal failure therapy machine using a Bluetooth® connection for sending patient blood pressure data. The renal failure therapy machine may combine the patient blood pressure data with renal failure therapy treatment data. The combined data may then be transmitted to a centralized hospital server for documentation in the patient's electronic medical record ("EMR").

The absence of device connectivity hinders the collection and transmission of patient and medical device data. In instances when devices cannot communicate with each other, a nurse or other clinician has to manually record the data and information from the machines/monitors. The nurse or clinician then has to locate a computer and enter the information directly into the patient's EMR. This process is time consuming, wastes valuable time the nurse or clinician could be treating patients, and is prone to transcription or data entry errors.

SUMMARY

The present disclosure provides a system, method, and apparatus for acquiring medical device data (e.g., medical information) and/or patient physiological data from medical devices that are not interconnected. In an example, a clinician has a tablet computer or smartphone (e.g., a portable device) with a camera. The clinician uses the camera on the portable device to record images of one or more medical device and/or of consumable item(s) associated with the medical device, before, during, or after a patient treatment such as, for example, a dialysis treatment. After all desired images are recorded, the clinician transports the portable device from the medical device(s) to a clinician computer. At the computer, the clinician selects a document, file, database, and/or template to which medical information from the images is to be entered as a keyboard entry from the portable device. The clinician may also use the computer to specify a location in the document, file, database, or template.

To facilitate the transfer of medical information from the recorded images, the clinician accesses an application (e.g., an App) stored on the portable device. The application uses a processor of the portable device to extract medical information text from at least one of the recorded images. In some embodiments, the application or processor uses optical character recognition ("OCR") to extract the text from the image. The clinician also uses the application of the portable device to establish a connection with a clinician computer. During the establishment of the connection, the portable device transmits one or more messages/files such that the clinician computer recognizes the portable device (or the application) as a keyboard input device. After the connection is established, the clinician provides an indication to the application that at least some of the extracted medical information is to be transmitted to the clinician computer. The indication causes the application to use the connection to transmit the selected or specified extracted medical information to the clinician computer as a keyboard input. In some instances, the clinician selects which of the extracted medical information is to be transmitted as a keyboard input. The application on the portable device accordingly operates as a virtual keyboard to enable the clinician to remotely enter data to a document, patient file, or patient medical template at the clinician computer.

The application on the portable device enables a clinician to record images of virtually any medical information displayed or provided by a medical device for entry at a clinician computer. The medical information may include medical device settings, medical device readings, or patient readings. The medical information may also include an identifier of a medical device, a consumable item, a patient, etc. The above-described clinician-assisted information entry process reduces data entry burdens placed on the clinicians and potential transcription errors.

In some embodiments, the application on the portable device is configured to guide an operator through a series or sequence of operations for recording one or more image, selecting extracted medical information for transmission, and transmitting the selected extracted medical device information as a keyboard input, etc. For example, the application may cause the portable device to display prompts that identify to an operator a type of medical device or a screen of a medical device to be imaged. The prompts may also instruct an operator regarding a sequence in which extracted medical information is to be transmitted as a keyboard input to a clinician computer.

Additionally, in some embodiments, the application on the portable device is configured to use data templates to organize extracted medical information. A data template may include definitions regarding locations, regions, labels, etc., of medical information within an image. The application uses the data template to identify the extracted medical information. Identification includes, for example, placing extracted medical information into data fields based on the location of the extracted medical information within an image or based on medical information that matches predetermined labels. The application enables an operator to select one or more data field such that the extracted medical information assigned to the selected data field is transmitted to a clinician computer as a keyboard entry.

In an example embodiment, a portable device transmits medical data or information to a clinician computer. The portable device includes a camera configured to record images, a memory storing the recorded images, and a display interface for displaying the images. The portable device also includes a processor configured to execute machine-readable instructions, which when executed, cause the processor to instruct the camera to record at least one of the images, extract medical data from the at least one image using an optical character recognition routine, establish a connection with a clinician computer such that the portable device is recognized by the clinician computer as a keyboard, and transmit at least some of the extracted medical data to the clinician computer as a keyboard input to the clinician computer.

In another embodiment, an application operates on a portable device to transmit medical information to a clinician computer. The application comprises machine-readable instructions, which when executed, cause the application to receive at least one image recorded by a camera of the portable apparatus and display the at least one image on a display interface of the portable apparatus. The machine-readable instructions, which when executed, also cause the application to use a processor of the portable apparatus to extract medical information from the at least one image and establish a connection with the clinician computer such that the portable device is recognized by the clinician computer as a keyboard. The machine-readable instructions, which when executed, further cause the application to use the processor of the portable apparatus to transmit at least some of the extracted medical information to the clinician computer as a keyboard input to the clinician computer.

In light of the technical features set forth herein, and without limitation, in a first aspect, a portable device for transmitting medical data to a clinician computer includes a camera configured to record images, a memory storing the recorded images, a display interface for displaying the images, and a processor configured to execute machine-readable instructions, which when executed, cause the processor to (i) instruct the camera to record at least one of the images, (ii) extract medical data from the at least one image using an optical character recognition routine, (iii) establish a connection with the clinician computer such that the portable device is recognized by the clinician computer as a keyboard, and (iv) transmit at least some of the extracted medical data to the clinician computer as a keyboard input to the clinician computer.

In a second aspect, which may be used with any other aspect described herein unless specified otherwise, the connection includes at least one of a Bluetooth® connection or a Zigbee® connection.

In a third aspect, which may be used with any other aspect described herein unless specified otherwise, the processor is configured to specify itself as being of at least one of (i) a universal serial bus ("USB") human interface device ("HID") class or (ii) a Bluetooth® HID profile to the clinician computer such that the portable device is recognized as the keyboard input by the clinician computer.

In a fourth aspect, which may be used with the third aspect in combination with any other aspect described herein unless specified otherwise, the processor is configured to transmit at least one device driver file including USB HID class information or Bluetooth® HID information to the clinician computer to establish the connection.

In a fifth aspect, which may be used with any other aspect described herein unless specified otherwise, the processor is configured to display a camera message via the display interface prompting an operator to use the camera to record the at least one image, determine, as part of the extracted medical data, a type of a medical device from the at least one recorded image, and enable the operator to select a portion of the extracted medical data for transmission to the clinician computer based on the determined type of the medical device.

In a sixth aspect, which may be used with the fifth aspect in combination with any other aspect described herein unless specified otherwise, the processor is configured to use the determined type of the medical device to determine whether a message is to be displayed, and if so, display a navigation message via the display interface prompting the operator to navigate to a specified window that is displayed by a screen of the medical device.

In a seventh aspect, which may be used with any other aspect described herein unless specified otherwise, the memory stores at least one data template for processing the at least one image, the data template configured to organize the extracted medical data.

In an eighth aspect, which may be used with any other aspect described herein unless specified otherwise, the processor is configured to cause the display interface to display a camera message that prompts an operator to use the camera to record, in the at least one image, an identifier of a medical device, the identifier including at least one of a quick-response ("QR") code, a barcode, a serial number, or a hardware number located on a housing of the medical device or the screen of the medical device.

In a ninth aspect, which may be used with the eighth aspect in combination with any other aspect described herein unless specified otherwise, the processor analyzes the identifier by at least one of decoding a pattern within the recorded image or performing optical character recognition on the identifier image.

In a tenth aspect, which may be used with any other aspect described herein unless specified otherwise, the processor is configured to enable the extracted medical data from the at least one image to be transmitted as a keyboard input to the clinician computer by selecting, via the display interface, at least a portion of the extracted medical data for transmission.

In an eleventh aspect, which may be used with any other aspect described herein unless specified otherwise, the processor is configured to display a verification message via the display interface prompting the operator to confirm that the extracted medical data matches data in the at least one image.

In a twelfth aspect, which may be used with any other aspect described herein unless specified otherwise, the at least one image is of a consumable item, the extracted medical data being consumable data, and wherein the processor is configured to transmit the consumable data to the clinician computer as a keyboard input.

In a thirteenth aspect, which may be used with the twelfth aspect in combination with any other aspect described herein unless specified otherwise, the consumable data includes data concerning at least one of a filter, a blood line set, a dialysis fluid concentrate container, a blood anticoagulant container, a medication container, a peritoneal dialysis cassette, a sorbent cartridge, or a drug infusion line set.

In a fourteenth aspect, which may be used with the twelfth aspect in combination with any other aspect described herein unless specified otherwise, the processor is further configured to prompt an operator to record the at least one image of the consumable item.

In a fifteenth aspect, which may be used with any other aspect described herein unless specified otherwise, the at least one image is of a medical device parameter setting, a medical device reading, or a patient reading, the extracted medical data being medical device parameter setting data, medical device reading data, or patient reading data, and wherein the processor is configured to transmit the medical device parameter setting data, the medical device reading data, or the patient reading data to the clinician computer as a keyboard input.

In a sixteenth aspect, which may be used with the fifteenth aspect in combination with any other aspect described herein unless specified otherwise, the medical device parameter setting, the medical device reading, or the patient reading is recorded from a medical device including at least a renal failure therapy machine, an infusion pump, an oxygen sensor, a respiratory monitor, a glucose meter, a blood pressure monitor, an electrocardiography ("ECG") monitor, a weight scale, or a heart rate monitor.

In a seventeenth aspect, which may be used with the twelfth aspect in combination with any other aspect described herein unless specified otherwise, the processor is further configured to prompt an operator to record the at least one image of the medical device parameter setting, the medical device reading, or the patient reading.

In an eighteenth aspect, which may be used with any other aspect described herein unless specified otherwise, the processor is further configured to assign a patient identifier to the extracted medical data, and wherein the patient identifier includes at least one of a quick-response ("QR") code, a text string, a barcode, a name, or a patient identifier located on a patient wristband.

In a nineteenth aspect, which may be used with any other aspect described herein unless specified otherwise, an application for operation on a portable device is configured to transmit medical data to a clinician computer, the application comprising machine-readable instructions, which when executed, cause the application to operate with a processor of the portable device to extract medical data from at least one image received from a camera of the portable device and displayed on a display interface of the portable device, operate with the processor of the portable device to establish a connection with the clinician computer such that the portable device is recognized by the clinician computer as a keyboard, and operate with the processor of the portable device to transmit at least some of the extracted medical data to the clinician computer as a keyboard input to the clinician computer.

In a twentieth aspect, which may be used with the nineteenth aspect in combination with any other aspect described herein unless specified otherwise, the application includes additional machine-readable instructions, which when executed, cause the application to operate with the processor to display a message via the display interface of the portable device prompting an operator to record the at least one image.

In a twenty-first aspect, which may be used with the nineteenth aspect in combination with any other aspect described herein unless specified otherwise, the application includes additional machine-readable instructions, which when executed, cause the application to receive a selection, via the display interface of the portable device, indicative of a portion of the extracted medical data, and transmit the selected portion of the extracted medical data to the clinician computer as a keyboard input to the clinician computer.

In a twenty-second aspect, which may be used with any other aspect described herein unless specified otherwise, a method for transmitting medical data to a clinician computer includes receiving, in an application operating on a portable device, at least one image recorded by a camera of the portable device, displaying the at least one image on a display interface of the portable device, extracting, via a processor of the portable device, medical data from the at least one image, establishing, using the application operating on the portable device, a connection with the clinician computer such that the portable device is recognized by the clinician computer as a keyboard, and transmitting, using the application operating on the portable device, at least some of the extracted medical data to the clinician computer as a keyboard input to the clinician computer.

In a twenty-third aspect, which may be used with the twenty-second aspect in combination with any other aspect described herein unless specified otherwise, establishing the connection with the clinician computer includes causing the portable device to emulate a keyboard with respect to a serial interface of the clinician computer.

In a twenty-fourth aspect, which may be used with the twenty-second aspect in combination with any other aspect described herein unless specified otherwise, the method further includes extracting, via the application, the extracted medical data using a data template that organizes the at least one image, and transmitting, using the application operating on the portable device, the extracted medical data to the clinician computer as a keyboard input to the clinician computer.

In a twenty-fifth aspect, which may be used with the twenty-fourth aspect in combination with any other aspect described herein unless specified otherwise, the data template is recorded by a camera on the portable device of a screen of the clinician computer.

In a twenty-sixth aspect, which may be used with the twenty-second aspect in combination with any other aspect described herein unless specified otherwise, the method further includes receiving a selection from the display interface indicative of (i) one of the at least one images, or (ii) a portion of the extracted medical data from the at least one image, and transmitting (i) the extracted medical data from the selected image, or (ii) the selected portion of the extracted medical data to the clinician computer as a keyboard input to the clinician computer.

In a twenty-seventh aspect, which may be used with the twenty-second aspect in combination with any other aspect described herein unless specified otherwise, the method further includes causing, using the application operating on the portable device, a speaker of the portable device to provide an announcement of at least a portion of the extracted medical data from the selected image, and receiving, using the application operating on the portable device, a validation indication that the announced extracted medical data is to be transmitted as the keyboard input.

In a twenty-eighth aspect, which may be used with the twenty-second aspect in combination with any other aspect described herein unless specified otherwise, the method further includes displaying a message prompting an operator to use the camera of the portable device to record the at least one image.

In a twenty-ninth aspect, any of the features, functionality and alternatives described in connection with any one or more of FIGS. 1 to 24 may be combined with any of the features, functionality and alternatives described in connection with any of the other one or more of FIGS. 1 to 24.

It is accordingly an advantage of the present disclosure to provide a medical data transfer device, system, and method that require little to no information technology setup or support.

In another advantage of the present disclosure, the medical data transfer device, system, and method operate with virtually any clinician or medical records software.

In a further advantage of the present disclosure, the medical data transfer device, system, and method enable the transfer of medical data from an image without an operator having to manually enter the data, thereby reducing the chances of a transcription error.

BRIEF DESCRIPTION OF THE FIGURES

FIGS. 10 to 20 are schematic diagrams illustrating an example workflow for populating the medical device template of FIG. 6 using images recorded by the portable device of FIGS. 1, 2, and 9, according to an example embodiment of the present disclosure.

DETAILED DESCRIPTION

General Information

Figure 1:
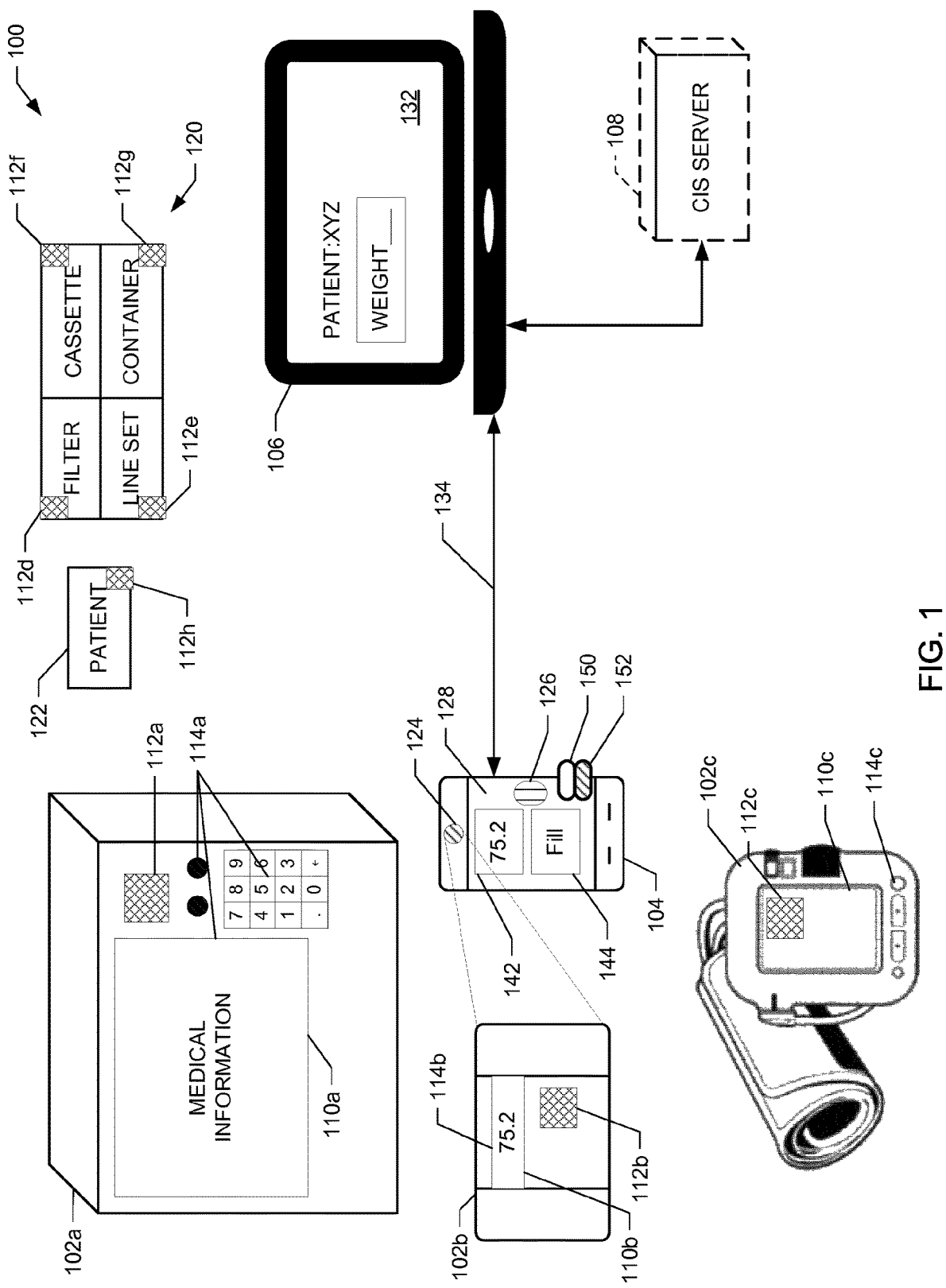
FIG. 1 is a schematic diagram illustrating a clinical system including a clinician computer and a portable device, according to an example embodiment of the present disclosure.

The present disclosure relates in general to a method, apparatus, and system for collecting medical information (e.g., medical device data or patient data), and more specifically, to a portable device configured to enter patient medical data as a keyboard entry to a separate computer. The example portable device is configured to obtain the patient medical data from one or more medical device connected to or otherwise related to the patient. To simplify the data collection process, the example portable device is configured to record one or more image of the one or more medical device associated with a particular patient and/or treatment. The portable device analyzes the images to identify patient medical data, which is then entered into a clinician computer.

In an embodiment, the portable device emulates a keyboard or otherwise becomes a keyboard input to enter medical information into a clinician computer. Emulation of a keyboard may include transmitting the medical information serially into documents, files, or databases of known clinician software or into a patient file or data fields of a patient medical template on a clinician computer. A clinician may specify where the information is to be entered prior to sending the medical information or sending a portion of the medical information. In one instance, a clinician may move a mouse cursor to a desired field, cell, document, or open file at the clinician computer, and then provide an instruction at the portable device to transmit the medical information. The clinician may specify the location using a mouse (or other input device) at the clinician computer. In other instances, the portable device may also emulate a mouse (or other data entry device) to enable a clinician to remotely select the field, document, and/or file for data entry. In yet other instances, the portable device remotely connects to the clinician computer to provide a display of a desktop screen of the clinician computer. The clinician may then select at the portable device which fields, files, and/or documents are to receive medical data. In some embodiments, the clinician may select at the portable device which medical information is to be transmitted, e.g., by touching a digital image having extracted medical information available for selection. The portable device sends the relevant medical information to the clinician computer, which is entered at the cursor specified location. The disclosed configuration accordingly enables the portable device to operate as a keyboard (or other data entry device) for the clinician computer.

The example method, apparatus, and system disclosed herein address known connectivity issues in medical facilities and/or patients' homes. Commonly, a clinic, such as a dialysis clinic, may have a plurality of medical devices including different renal failure therapy machines, weight scales, and blood pressure monitors. Oftentimes, the medical devices support wireless and/or wired connectivity. However, it is difficult and time consuming for a clinician or patient to connect a portable device to the appropriate medical devices to acquire patient medical information. For example, a clinic may contain tens of patients concurrently undergoing treatment. For a wireless information transfer, a clinician has to operate a pairing routine to connect to the desired medical device, download the information into a patient file, and then begin a disconnection routine. The clinician has to repeat this sequence for each device for each patient.

In addition, the clinician has to be keenly aware of which device is being paired. Otherwise, the clinician may connect to the wrong medical device. To ensure the correct pairing in known systems, a clinician has to match a wireless identifier of a medical device (displayed on a screen of the portable device for pairing) to the identifier that is physically located on the medical device. In a busy clinic, it is easy for a clinician to become distracted or rushed, thereby increasing the chances for an undesired device pairing. In other instances, the portable device may be concurrently paired or connected to all medical devices in a facility. However, the clinician still has to select the proper device for obtaining patient medical information.

In other known environments, connectivity is a luxury. For example, many renal failure therapy machines or other medical devices may not have the capability to wirelessly connect directly to a portable device and/or a network. Alternatively, a clinic may contain only a small number of devices with the ability to connect or devices with different connection configurations. However, for the ease of workflow, clinicians often bypass the connectivity features and manually record patient medical information into a notebook for later entry into a computer system. It may be too burdensome, for instance, to memorize the different connection requirements for different medical devices. Moreover, relatively basic medical devices such as weight scales and blood pressure monitors may not have device connectivity capabilities.

To overcome the lack of connection capabilities or complexity of the connections, the example system, method, and apparatus disclosed herein enables a clinician or patient to record images or pictures of the medical devices using a portable device and to transfer medical information from those images to a clinician or other separate computer. Generally, even the most basic portable devices have adequate cameras for recording, for example, images of a screen of a medical device, images of an identifier on a medical device, and/or images of the medical device itself. The images are analyzed to extract or otherwise determine medical information (e.g., medical device data). The extracted medical information is transmitted to a remotely located computer (e.g., a clinician computer) to populate a file and/or a patient medical template, which may be stored as an electronic medical record ("EMR"). The clinician may be educated and left to decide which images to record. Additionally or alternatively, the portable device may display or otherwise provide messages prompting the clinician regarding the images or pictures that need to be recorded and thereafter guide the clinician though a sequence or routine to ensure substantially all medical information for a given therapy or treatment is transmitted as a keyboard entry to a clinician computer.

Reference is made throughout to medical devices, medical device data, medical information, and patient data. Medical devices include devices configured to provide a treatment to a patient such as a renal failure therapy machine or an infusion pump. Medical devices also include devices configured to record physiological data related to a patient. Examples include an oxygen sensor, a respiratory monitor, a glucose meter, a blood pressure monitor, an ECG monitor, a weight scale, and a heart rate monitor.

Medical information or data includes medical device data and patient data, which may refer to data or information created by, generated by, or otherwise related to medical devices, patients, and/or consumable items used by medical devices. For instance, the medical information includes prescription or programming information used by a medical device to administer a treatment. The medical information also includes treatment status information, such as a volume of fluid infused, an amount of ultrafiltration ("UF") removed from a patient, and/or alarms or alerts. Medical information also includes sensed data such as fluid pressure, flowrate, conductivity, concentration, and temperature. Patient data includes sensed patient physiological information such as patient blood pressure, weight, heart rate, etc. The medical information may be displayable on a screen, provided by a physical scale, or printed on a label that can be recorded in an image. Accordingly, medical device data or medical information includes a medical device setting, a medical device reading, and/or a patient reading.

Medical information also refers to information contained on an identifier attached to a patient or treatment consumable item. Specifically, the medical information may include information conveyed by an identifier of a patient provided on a patient wristband for identifying a patient. Medical information also includes information regarding a consumable item, which may identify a consumable item type, a consumable item model, and/or properties of a consumable item, such as a level of dextrose in a supply bag of renal failure therapy solution. Consumable items may include, for example, a renal failure therapy filter, a blood line set, sorbent cartridge, a dialysis solution concentrate container, a blood anticoagulant container, a medication container, a peritoneal dialysis disposable cassette, a drug infusion line set, etc.

Reference is made in multiple instances herein to patient medical templates. As provided herein, a patient medical template includes or specifies data fields for documenting a certain medical treatment or condition of a patient. For example, a patient medical template for a renal failure therapy may include data fields for a patient's name, date of treatment, amount of UF removed, a patient weight, and a patient blood pressure. A completed patient medical template is stored to a database as an EMR, which enables a patient's treatments to be monitored and documented. It should be appreciated that templates are not required for the systems, methods, and apparatuses of the present disclosure and that not all medical information is stored to a patient medical template.

Reference is further made in multiple instances herein to relevant medical information or relevant medical device data. Generally, images include extracted text comprising medical information. In some instances, not all of the extracted medical information is to be transmitted as a keyboard entry. Instead, only certain medical information in a recorded image is needed for entry. Relevant medical information or relevant medical device data refers to medical device data or medical information that is identified or selected for transmission to a clinician computer as a keyboard entry or to populate a patient template.

II. System Information

FIG. 1 shows a schematic diagram that is illustrative of a clinical system 100, according to an embodiment of the present disclosure. The example clinical system 100 includes medical devices 102a to 102c, a portable device 104, and a clinician or clinical information system ("CIS") computer 106. In some embodiments, the computer 106 is communicatively coupled to a CIS server 108 via a local or wide area network connection. In addition, in some embodiments, the connection between the computer 106 and the CIS server 108 is via a hospital information system.

The example medical devices 102a to 102c are configured to provide a treatment to a patient and/or record physiological data related to the patient. Each of the medical devices 102a to 102c includes a screen 110 configured to display medical device data. In some embodiments, screen 110 may be replaced with a physical scale, dial, or other device configured to convey physiological information. For example, instead of screen 110c, blood pressure medical device 102c may include a mechanical dial that points to a blood pressure value on a scale based on a measured patient blood pressure.

Each of the medical devices 102a to 102c also includes an identifier 112 configured to store a unique identification number. Identifier 112 may code, for example, an assigned device number, a serial number, a hardware number, a model number, and/or a device type of the medical device 102a to 102c. For example, identifier 112a of renal failure therapy medical device 102a may store an assigned device number. The portable device 104 reads identifier 112a to determine, for example, a medical device type for subsequent analysis and identification of medical device data in images recorded from the screen 110a. In some embodiments, identifier 112 may more generally indicate a model or type of medical device. For example, identifier 112b may indicate that device 102b is a weight scale and/or indicate a model number of a weight scale.

The identifier 112 may include machine readable markings such as, for example, a barcode or a quick-response ("QR") code. Identifier 112 may also include human-readable text, such as a serial number, asset number, or hardware number. In some embodiments, identifier 112 may be printed to an article physically attached to a housing of medical device 102a to 102c, such as identifier 112a shown for the renal failure therapy medical device 102a. Additionally or alternatively, identifier 112 may be displayed on screen 110 of medical device 102a to 102c. For example, a clinician may select a control interface 114 to cause medical device 102a to 102c to display a window with the identifier 112 on the screen 110. In yet other embodiments, identifier 112 may included within a radio frequency ("RF") microchip, such as an RFID chip or NFC chip.

Medical devices 102a to 102c may also include one or more control interface 114 for providing control instructions. Control interfaces 114 may include buttons or a control panel, as shown for medical devices 102a and 102c. The control interfaces 114 may also include a touchscreen, as shown for medical devices 102a and 102b. As described in more detail below, control interfaces 114 may be configured to enable a user to navigate to a certain window or data display of the medical device 102a. Control interfaces 114 may also provide instructions for operating or controlling medical devices 102.

The example clinical system 100 of FIG. 1 may include a plurality of medical devices. For illustration, FIG. 1 shows a renal failure therapy medical device 102a, a weight scale medical device 102b, and a blood pressure monitor medical device 102c. In other embodiments, the clinical system 100 can include other types of medical devices including an infusion pump (e.g., a syringe pump, a linear peristaltic pump, a large volume pump ("LVP"), an ambulatory pump, multi-channel pump), an oxygen sensor, a respiratory monitor, a glucose meter, a blood pressure monitor, an electrocardiogram ("ECG") monitor, a weight scale, and/or a heart rate monitor. Further, in some embodiments, the clinical system 100 may include a plurality of each type of the medical devices. For example, the clinical environment 100 may include twenty renal failure therapy medical devices 102a, ten weight scale medical devices 102b, and eight blood pressure monitor medical devices 102c.

Example renal failure therapy medical device 102a includes any hemodialysis, hemofiltration, hemodiafiltration, continuous renal replacement therapy ("CRRT"), or peritoneal dialysis ("PD") machine. A patient, undergoing a renal failure therapy is, for example, connected to the renal failure therapy medical device 102a, where the patient's blood may be pumped through a blood set operated by the machine. The blood passes through a dialyzer of the blood set, which removes waste, toxins and excess water from the blood. The cleaned blood is returned to the patient. In PD, treatment fluid is delivered to and removed from a patient's peritoneal cavity to remove toxins and excess water.

CRRT is a dialysis modality used typically to treat emergency or critically ill, hospitalized patients in an intensive care unit who develop acute kidney injury ("AKI"). Unlike chronic kidney disease, which typically advances slowly over time, AKI often occurs temporally in hospitalized patients and may last a few hours to a few days.

Hemodialysis is a renal failure treatment in which waste from the blood is diffused across a semi-permeable membrane. During hemodialysis, blood is removed from the patient and flows through a semi-permeable membrane assembly (dialyzer), where the blood flows generally counter-current to dialysis solution flowing on the other side of the semipermeable membrane. In the dialyzer, toxins from the blood travel across the semi-permeable membrane and exit the dialyzer as used dialysis solution (dialysate). The cleaned blood, having flowed through the dialyzer, is then returned to the patient.

The renal failure therapy medical device 102a can alternatively be a hemofiltration machine. Hemofiltration is another renal failure treatment, similar to hemodialysis. During hemofiltration, a patient's blood is also passed through a semipermeable membrane (a hemofilter), wherein fluid (including waste products) is pulled across the semipermeable membrane by a pressure differential. This convective flow brings certain sizes of molecular toxins and electrolytes (which may be difficult for hemodialysis to clean) across the semipermeable membrane. During hemofiltration, a replacement fluid is added to the blood to replace fluid volume and electrolytes removed from the blood through the hemofilter. Hemofiltration in which replacement fluid is added to the blood prior to the hemofilter is known as pre-dilution hemofiltration. Hemofiltration in which replacement fluid is added to the blood after the hemofilter is known as post-dilution hemofiltration.

The renal failure therapy medical device 102a can further alternatively be a hemodiafiltration machine. Hemodiafiltration is a further renal failure treatment that uses hemodialysis in combination with hemofiltration. Blood is pumped through a dialyzer, which accepts fresh dialysis fluid, unlike a hemofilter. With hemodiafiltration, however, replacement fluid is delivered to the blood circuit as with hemofiltration. Hemodiafiltration is accordingly a neighbor of hemodialysis and hemofiltration.

The renal failure therapy medical device 102a can still further alternatively be a peritoneal dialysis machine. Peritoneal dialysis uses a dialysis solution, which is infused into a patient's peritoneal cavity via a catheter. The dialysis solution contacts the peritoneal membrane of the patient's peritoneal cavity. Waste, toxins and excess water pass from the patient's bloodstream, through the peritoneal membrane and into the dialysis solution due an osmotic gradient created by the solution over a patient dwell period. Spent dialysis solution is drained from the patient, removing waste, toxins and excess water from the patient. This cycle is repeated.

An example peritoneal dialysis machine, operating as the renal failure therapy medical device 102a of FIG. 1, may perform various types of additional peritoneal dialysis therapies, including continuous cycling peritoneal dialysis ("CCPD"), tidal flow automated peritoneal dialysis ("APD"), and continuous flow peritoneal dialysis ("CFPD").

APD machines perform drain, fill, and dwell cycles automatically, typically while the patient sleeps.

Peritoneal dialysis dialysate may include a solution or mixture that includes between 0.5% and 10% dextrose (or more generally glucose), preferably between 1.5% and 4.25%. Peritoneal dialysis dialysate may include, for example, Dianeal®, Physioneal®, Nutrineal®, and Extraneal® dialysates marketed by the assignee of the present disclosure. The dialysate may additionally or alternatively include a percentage of icodextrin.

In both hemodialysis and peritoneal dialysis, "sorbent" technology can be used to remove uremic toxins from waste dialysate, re-inject therapeutic agents (such as ions and/or glucose) into the treated fluid, and reuse that fluid to continue the dialysis of the patient. One commonly used sorbent is made from zirconium phosphate, which is used to remove ammonia generated from the hydrolysis of urea. Typically, a large quantity of sorbent is necessary to remove the ammonia generated during dialysis treatments.

The example weight scale medical device $102b$ includes any device configured to measure a mass of a patient or treatment component. For example, the weight scale medical device $102b$ may measure a patient weight before, during, and/or after a renal failure therapy treatment. Additionally or alternatively, weight scale medical device $102b$ may measure a supply or drain bag for tracking a renal failure therapy. Specifically, weight scale medical device $102b$ may be used to measure an amount of UF removed or an amount of fluid provided to a patient. Weight scale medical device $102b$ may display a digital value indicative of weight. Alternatively, weight scale medical device $102b$ may display a physical scale that aligns with a marker to indicate a measured weight. In some embodiments, weight scale medical device $102b$ may store weight values before, during, and/or after treatment in separate windows such that clinician input is required to view all the values when medical device data is recorded.

Example blood pressure medical device $102c$ includes any device configured to measure a blood pressure of a patient. For example, blood pressure medical device $102c$ may measure a patient blood pressure before, during, and/or after a renal failure therapy treatment. Blood pressure medical device $102c$ may display a digital value indicative of a patient's blood pressure. Alternatively, blood pressure medical device $102c$ may display a physical scale with a dial that aligns with a numerical value to indicate a measured blood pressure. In some embodiments, blood pressure medical device $102c$ may store blood pressure values before, during, and/or after treatment in separate windows such that clinician input is required to view all the values when medical device data is recorded.

In addition to obtaining medical information (e.g., medical device data) from the medical devices $102a$ to $102c$, example portable device 104 may also obtain medical information from a patient and/or therapy consumable items 120. FIG. 1 shows an example of consumable items 120, which include, for example, a renal failure therapy medical device filter, a disposable cassette, a blood line set, a drug delivery line set, and a container (e.g., a dialysis solution concentrate container, a blood anticoagulant container, a medication container, and/or a water purification container). Consumable items 120 may also include a sorbent cartridge or any other disposable or material supply for a medical treatment. Consumable items 120 each include an identifier $112d$, $112e$, $112f$, and $112g$, which is configured to provide medical information in the form of consumable information or consumable data. For example, the identifiers $112d$ to $112g$ may include information identifying a type of consumable item, a serial number, and/or properties of the consumable item. In some instances, consumable item 120 may also include a label containing medical device data such as chemical composition properties. A clinician records images of identifiers $112d$ to $112g$, images of labels on the consumable items 120, and/or images of the consumable items 120 themselves to document materials used during a treatment.

Example portable device 104 is also configured to obtain medical information from a patient 122 as patient information. Specifically, portable device 104 may image or otherwise scan an identifier $112h$ on a patient wristband or tag to obtain medical device data related to the patient 122. Such information may include a patient name, a patient identifier, a birth date, a gender, and/or a treatment type that patient 122 is undergoing.

The example portable device 104 of FIG. 1 is configured to record images of the medical devices $102a$ to $102c$ to obtain medical information. Portable device 104 extracts the medical information from the images and transmits this information to the computer 106. To record images, portable device 104 includes at least one camera 124. The portable device 104 also includes a medical data application 126 programmed or configured to operate with a processor 150 and memory 152 of portable deice 104 to extract text as medical information from the images. The images and/or the extracted medical information are displayed on a screen 128 of portable device 104. Medical data application 126 may also process the extracted data for transmission to populate a file, document, and/or medical device template at computer 106. Portable device 104 may include any tablet computer, smartphone, laptop, smart-eyewear, smartwatch, etc., and combinations thereof. In some embodiments, portable device 104 may include a radio-frequency identification ("RFID") reader and/or a near-field communication ("NFC") reader to scan and obtain information from corresponding RFID or NFC tag identifiers 112. Example portable device 104 and medical data application 126 are described in further detail below.

The portable device 104 includes processor 150 to execute one or more institution stored in memory 152 to perform certain operations or routines. As described herein, the processor 150 operates in conjunction or cooperation with medical data application 126 to receive images from cameras 124, extract text from the images, provide for selection of the extracted text as medical information, and transmit the selected medical information as a keyboard entry to computer 106. Processor 150 may comprise digital and analog circuity structured as a microprocessor, application specific integrated circuit ("ASIC"), controller, etc. Further processor 150 may comprise a single processor or multiple processors in communication with each other. In some embodiments, processor 150 or portions of processor 150 may be remote from portable device 104 (e.g., located in a cloud computing environment).

Memory 152 stores instructions, which for example, specify processes performed for the medical data application 126 on processor 150 and specify how medical data application 126 operates or interfaces with, for example, camera 128, screen 126, and network connections. Memory 152 includes a volatile or non-volatile storage medium. Further, memory 152 may include any solid state or disk storage medium.

The example clinician or CIS computer 106 of FIG. 1 is configured to operate a data entry program, such as a document program, a spreadsheet program, a text entry program, a patient medical template program, or combinations thereof. The programs are configured to display documents, worksheets, templates, or combinations thereof that receive text provided, for example, from a keyboard. In some embodiments, the documents, worksheets, templates or combinations thereof may include data fields designated for specific medical information. The programs on the clinician computer 106 may include off-the-shelf clinician software or be customized as part of system 100 of the present disclosure. If provided as off-the-shelf software, it should be appreciated that very little internal information technology ("IT") support is required to implement system 100 and its associated methodology.

Computer 106 may include any type of computer, such as a tablet computer, a laptop computer, a desktop computer, a workstation, a server, etc. or combinations thereof. Computer 106 in the illustrated embodiment includes a screen 132 for displaying, for example, documents, worksheets, templates and combinations thereof for receiving medical information. CIS computer 106 may be communicatively coupled to portable device 104 via a connection 134. In some embodiments, connection 134 is a wired connection, such as through universal serial bus ("USB"), micro-USB, RS-2232, a Lightening® connection, a high-definition multimedia interface ("HDMI") connection, or combinations thereof. In other examples, connection 134 may comprise a wireless connection such as Bluetooth®, Zigbee®, etc. or combinations thereof. In yet other examples, connection 134 may be provided over a local area network ("LAN"), a wireless LAN, a Wi-Fi connection, or combinations thereof Connection 134 may be persistent between the portable device 104 and the computer 106 to enable, for example, medical information to be transmitted after it is extracted from one or more images. Alternatively, connection 134 may be periodic. For example, a clinician may use portable device 104 to record images of medical devices 102. After the medical device data is obtained, the clinician establishes the connection 134 (e.g., connects a USB cable or performs a Bluetooth® pairing) to provide for the transfer of the medical information to computer 106. It should be appreciated that the configuration illustrated in FIG. 1 needs only one communication connection in one embodiment, which is the connection 134 between the portable device 124 and the computer 106. Such a signal connection is relatively easy to establish and maintain compared to connecting the portable device 104 to the medical devices 102.

The example CIS server 108 of FIG. 1 is configured to provide operations for a medical network and more generally, system 100. CIS server 108 may be connected to other computers, smartphones, servers, etc., within a medical network or securely connected to a medical network. CIS server 108 may manage the storage and retrieval of patient EMRs or prescriptions for the other devices. The CIS server 108 may also analyze medical device data in EMRs to determine if an alarm and/or alert is to be transmitted to other connected devices. The CIS server 108 may further provide computer 106 with patient medical templates for obtaining medical device data. Although it is envisioned that CIS server 108 resides in a same building or complex as computer 106, in some embodiments, server 108 may alternatively reside remote from computer 106 and communicate via a wide area or Internet connection. Also, computer 106 may be located locally or remotely with respect to medical devices 102*a* to 102*c*. For example, the clinician may record an image using portable device 104 at a clinic. The clinician then travels with the portable device 104 to a remote location having computer 106 to perform the transfer of medical information.

III. Keyboard Emulation Embodiment

In some embodiments, the connection 134 of FIG. 1 is configured to enable the portable device 104 to emulate or otherwise operate as a keyboard with respect to computer 106. In these embodiments, the connection 134 may include a wireless connection comprising at least one of a Bluetooth® connection, a Zigbee® connection, or a wireless universal serial bus ("USB") connection. Additionally or alternatively, the connection may comprise a wired USB connection, a micro-USB connection, an RS-2232 connection and/or a Lightening® connection.

The example medical data application 126 of portable device 104 causes processor 150 to establish, through the connection 134, the portable device 104 as a keyboard connected to computer 106. In other words, the medical data application 126 operates as a keyboard emulator with respect to computer 106. In some embodiments, after the connection 134 is made, the medical data application 126 causes processor 150 to transmit one or more message that specifies or establishes portable device 104 as being a computer peripheral such as, for example, being in a universal serial bus ("USB") human interface device ("HID") class. The one or more message may include a device driver file that provides USB HID class information to establish the portable device as a keyboard. In other embodiments, Bluetooth® HID class information is transmitted.

The HID class connection that medical data application 126 creates between the portable device 104 and computer 106 provides medical data application 126 with an input endpoint at computer 106 that communicates keystrokes. The endpoint includes, for example, a software interface and corresponding device driver that enables an operating system of the clinician computer 106 to receive communications from the medical data application 126 (via the processor 150). The keystroke communication enables text, including medical information, to be transmitted to computer 106 as a keyboard input, e.g., as though the portable device 104 is a keyboard relative to computer 106. The text may be transmitted serially and/or provide for key rollover to communicate medical device data in one or more message across the connection 134 from the portable device 104 to computer 106. For example, the medical data application 126 may cause processor 150 to transmit medical information using 6-key rollover and/or n-key rollover to improve data throughput.

In an embodiment where the portable device 104 is established as a USB HID, the medical data application 126 is configured to convert text provided by a user or identified in one or more images into ASCII inputs. The medical data application 126 then converts the ASCII inputs to HID scan codes, which are placed within one or more USB packets for transmission. The clinician computer 106 receives the USB packets at a device driver communicatively coupled to an I/O port. The device driver of the clinician computer 106 recovers and converts the HID scan codes to standard ASCII values.

In an embodiment where the portable device 104 is established as a Bluetooth® HID, the medical data application 126 is configured to convert text provided by a user or identified in one or more images into ASCII inputs. The medical data application 126 then converts the ASCII inputs to HID scan codes, which are placed within one or more Bluetooth® L2CAP packets for wireless transmission. The clinician computer 106 receives the Bluetooth® L2CAP packets at a Bluetooth® interface. The interface of the clinician computer 106 recovers and converts the HID scan codes to standard ASCII values.

The example medical data application 126 is configured to use medical information extracted from one or more image as keyboard entry text. The medical data application 126 uses processor 150 on portable device 104 to transmit text from the medical information to an input endpoint that is recognized by computer 106 as a keyboard input. For the transmission, medical data application 126 causes processor 150 of portable device 104 to transmit serially text from the medical information (individually or in a string of characters) such that an order of transmission provides an order in which the data is received and entered into a document, file, or template. In some embodiments, a clinician selects a desired order or desired portion of the text for entry to a selected location in a document, file, database, etc. of clinician software at computer 106.

Figure 2:
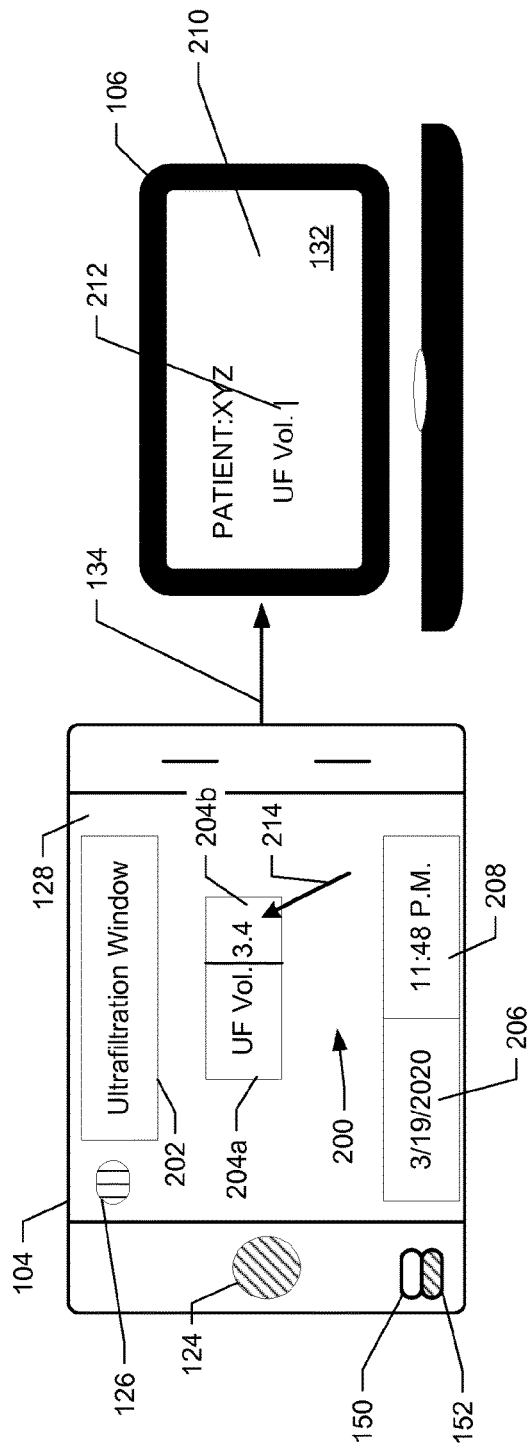
FIGS. 2 and 3 show diagrams that illustrate a transfer of medical device data from the portable device to a computer, according to an example embodiment of the present disclosure.

FIG. 2 shows a diagram that illustrates the transfer of the medical information from the portable device 104 to computer 106. In this example, the medical data application 126 has caused portable device 104 to establish connection 134 with the computer 106 and transmit one or more message causing the computer 106 to register or designate the portable device 104 as a keyboard input device. In the illustrated example, the medical data application 126 has received and processed an image of medical device 102a. The image includes medical information displayed by screen 110a of the medical device 102a. During processing of the image, the medical data application 126 uses processor 150 of portable device 104 to perform a routine (e.g., an OCR routine) that converts portions of the recorded image into text (e.g., ASCII characters). In some examples, the medical data application 126 may be configured to accept a selection of text from an image. The selection may include text or groups of text. To select text, a clinician may use cursor 214 or touch screen 128 to indicate text for selection. The selection of the text provides an indication to the medical data application 126 that the selected text is relevant medical information that is to be transmitted to computer 106.

In some instances, the medical data application 126 may organize or arrange proximate text into data fields, such as data fields 202 to 208 of FIG. 2. The medical data application 126 may also provide a graphical representation of the data fields 202 to 208. Instead of selecting text, a clinician selects one or more of data fields 202 to 208 to specify which of the text is to be transmitted to computer 106. For example, in the illustrated embodiment, the medical data application 126 operates with processor 150 of portable device 104 to make at least some of the data fields 202 to 208 selectable by a clinician. Selection of a data field by a clinician causes medical data application 126 to operate with processor 150 of portable device 104 to send relevant medical information (e.g., text) associated with the selected data field to computer 106 as keyboard entry text.

In some embodiments, the medical data application 126 causes the processor 150 to provide an audio output of at least some of the text extracted from an image. The medical data application 126 may, for example, use a text-to-speech algorithm to create audio that is indicative of the extracted text. The medical data application 126 causes the processor 150 of the portable device 104 to transmit the audio via a speaker to enable a clinician to hear a read-out or announcement of the extracted text. In these embodiments, the medical data application 126 may include a validate or "confirm" and "incorrect" buttons displayed on the screen 128 of the portable device 104 that enables a clinician to provide an indication that the extracted information is correct or incorrect. If the clinician provides an indication that the extracted text is correct, the medical data application 126 causes the processor 150 to transmit extracted text to the computer 106 via a keyboard emulation connection. If the medical data application 126 receives an indication that the extracted text is incorrect, the medical data application 126 may display a prompt for a clinician to enter the correct information and/or a prompt to record another image.

An additional "repeat" button may be provided on the screen 128 of the portable device 104 that enables the clinician to cause the audio message to be played again in case the message is not heard correctly. The medical data application 126 may be synched with the volume control of portable device 104, such that the audio message may be played more loudly in busy areas of a clinic for example.

In some instances where the medical data application 126 partitions the extracted text into separate fields, the medical data application 126 may transmit separate audio messages for each field to provide for individual validation by the clinician. In these instances, the medical data application 126 may disregard text for which a validation confirmation is not provided and only transmit extracted text for which a validation is received.

Additionally or alternatively, the medical data application 126 is configured to receive audio inputs from a clinician via a microphone on the portable device 104. In some instances, the medical data application 126 is configured to receive audio inputs instead of or in furtherance of a visual image capture of a medical device 102. The medical data application 126 causes the processor 150 to use a speech-to-text algorithm to convert the audio inputs into text. The medical data application 126 may display the text for validation by the clinician before transmitting the text as medical information to the computer 106 via the keyboard emulator. In some instances, the medical data application 126 may display or provide an audio prompt indicating that information is needed from the clinician. The medical data application 126 may cause the processor 150 of the portable device 104 to activate the microphone after the prompt is displayed and/or announced.

In an example, FIG. 2 shows that a clinician has opened a document 210 shown on screen 132 of computer 106. In addition, the clinician has selected data field 204a on portable device 104, which has caused the medical data application 126 to operate with processor 150 of portable device 104 to serially transmit the selected medical information, e.g., "UF Vol.", as text from the portable device 104 to computer 106. After receiving the selected medical information, computer 106 enters the received medical information corresponding to "UF Vol." into the document 210 as text. The medical information of "UF Vol." is placed in the document 210 at a location of cursor 212, which was specified by the clinician.

Figure 3:
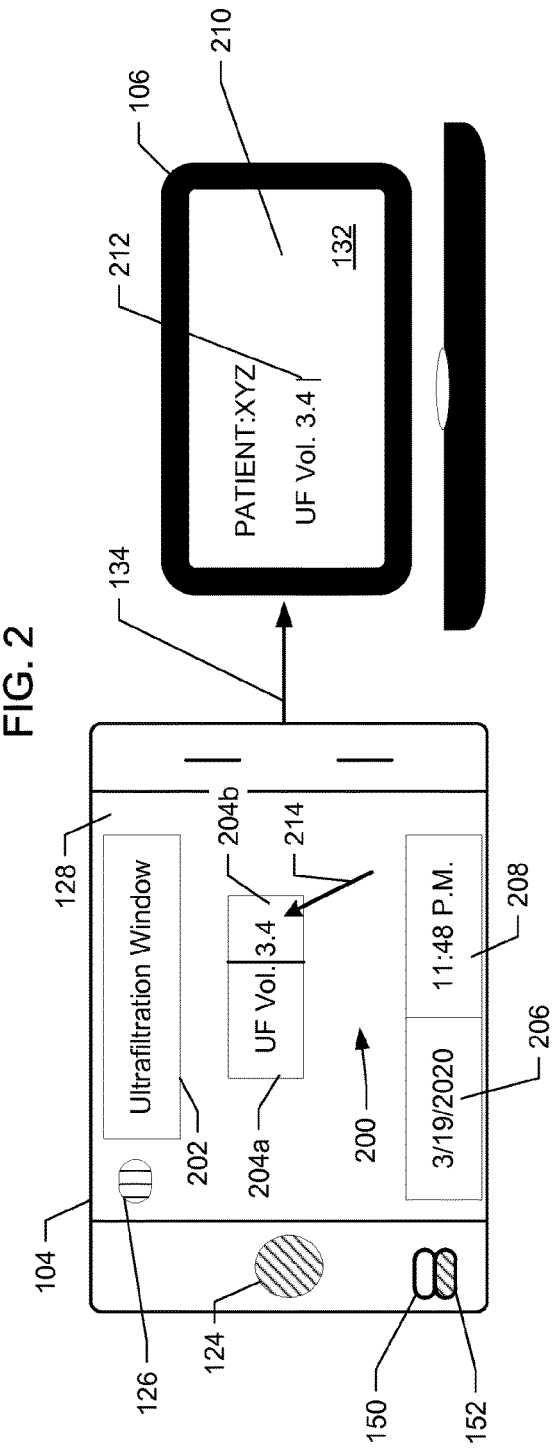

Next, the clinician moves cursor 212 to the left of the "UF Vol." text in the document 210 (e.g., using a mouse of computer 104 or a spacebar entry from portable device 104). The clinician then instructs medical data application 126 to operate with processor 150 of portable device 104 to transmit the corresponding medical information of "3.4" by selecting data field 204b at the portable device 104. The selection may be made using cursor 214 at the portable device 104 and/or using a touchscreen. The selection causes medical data application 126 to serially transmit the relevant medical information of "3.4" to computer 106, where it is entered as keyboard text at cursor 212 (as shown in FIG. 3). The clinician may select additional data fields 202 to 208 from the portable device 104 to continue transmission of the displayed medical device data.

It should be appreciated that the above-described configuration shown in FIGS. 2 and 3 operates with the clinician located at computer 106 while holding portable device 104 at the same time. It should be appreciated that document 210 may already display text such as "UF Vol." so that the clinician does not have to transfer such text from portable device 104, and so that the clinician knows where to point cursor 212 to enter the corresponding value of "3.4". It should also be appreciated that the process just described affords built-in accuracy checks by the clinician who does not have to remember and correctly transcribe the value, just the parameter to which the value belongs.

The example described above in connection with FIGS. 2 and 3 is for one recorded image. In some instances, a clinician may record multiple images. For instance, a clinician may navigate between multiple screens 110 on a medical device 102a to 102c and/or record images from different medical devices. The medical data application 126 may be configured in a number of different ways to enable a clinician to transfer relevant medical information from the portable device 104 to computer 106. For example, the medical data application 126 may be configured such that the clinician performs a transfer after each image is recorded. In another embodiment, the clinician may select data fields from an image, which are then placed in a queue by the medical data application 126. The medical data application 126 transmits the queued medical device data after connection 134 to computer 106 is established and, optionally, after a destination document, file, and/or template is selected at computer 106.

In other embodiments, the medical data application 126 is configured to store and/or compile recorded medical images. Then, after the clinician moves to computer 106, the medical data application 126 is configured to permit the clinician to browse through the recorded images for selective transfer to computer 106. In an example, the clinician may use cursor 212 to select a location in a document, file, and/or template of clinician software. The clinician then uses the medical data application 126 to scroll though the recorded images. Next, the clinician uses the medical data application 126 to select text and/or data fields for transmission as a keyboard entry to computer 106. The clinician then repeats the data entry process by moving cursor 212 to the next desired location and then selecting text and/or data fields from the same or multiple images. In such embodiments, the medical data application 126 operates processor 150 to access one of its algorithms, which guides or otherwise prompts the clinician as to which relevant medical information is to be obtained through imaging and/or transmitted to computer 106. In some instances, the prompts may provide an ordered sequence for acquiring and/or transmitting the relevant medical information, as described below in connection with FIGS. 5 to 23.

In some embodiments, medical data application 126 uses a data template for organizing or other wise deciphering extracted text from an image. The medical data application 126 determines or otherwise selects one or more data template for establishing a context for the medical information based, for example, on a position of the medical device data within the image and/or labels/keywords included within the medical device data. To determine a data template, the example medical data application 126 may cause processor 150 to prompt a clinician to specify a medical device type from which an image was recorded. Additionally or alternatively, the medical data application 126 may cause processor 150 to enable a clinician to select a medical device template. In yet other embodiments, a clinician may first record an image of an identifier 112 (e.g., an identifier image), which is used by the medical data application 126 to determine a type, model, etc. of the medical device 102. The medical data application 126 then causes processor 150 to select a data template that corresponds to the type, model, screen, etc. of the medical device 102.

In some embodiments, the medical data application 126 causes processor 150 to prompt a clinician to record an image of screen 132 of computer 106. The screen 132 may be displaying a data template of labeled fields that are to be populated with medical information. The medical data application 126 causes processor 150 to extract text within the recorded image that identifies with or corresponds to the one or more fields displayed on the screen 132 of computer 106. The extracted text is used by the medical data application 126 as a data template or for selecting a data template to enable text recorded in an image of a medical device to be identified as medical information for transmission to the computer 106.

For example, the screen 132 in FIG. 1 displays field label "Weight" which is adjacent to a numeric field for entering a patient's weight. Recording an image of the screen 132 causes the medical data application 126 to use the processor 150 to extract the "Weight" text from the image using an OCR operation. The medical data application 126 causes processor 150 to use the "Weight" text as a data template and/or for selecting a weight scale data template. In this manner, the computer 106 not only receives medical information from the medical data application 126 but also provides one or more prompts used for selecting or identifying which medical information is needed.

In some examples, the medical data application 126 may use units related to one or more fields to select a data template. For example, the field label "Weight" may correspond to a patient weight or an ultrafiltration weight. The medical data application 126 may analyze the units adjacent to the field to determine, for example, the "Weight" corresponds to a patient weight if the units are represented as kilograms and ultrafiltration weight if the units are represented as grams. Additionally or alternatively, the medical data application 126 may compare values within the extracted text to determine a data template. For example, values between a range of 55 kg and 90 kg may correspond to a patient weight while values less than 55 or 30 kg correspond to ultrafiltration weight. In yet other examples, the medical data application 126 may search for extracted text that provides an indication of a which data template should be selected, such as a model name or model number of a medical device or other information displayed on a screen of a medical device that is indicative of the data displayed.

The data templates define or specify data fields of certain medical information. The data fields may be defined based on a position or relative position within in image. The data fields may also be defined based on keywords and/or labels. In the example of FIG. 2, the medical data application 126 causes processor 150 to use a data template that identifies data fields 202, 204a, 204b, 206, and 208. The medical data application 126 may cause processor 150 to apply the data fields to a text-recognized image using relative location and/or labels. For example, the medical data application 126 may determine that data field 202 is specified as corresponding to label "Ultrafiltration Window." The medical data application 126 causes processor 150 to search for text within the image that matches the label and applies the data field 202 to the text. In another example, data field 204a may specify a location relative to data field 202 and/or include a label "UF Vol." The medical data application 126 causes processor 150 to search for text within the image that matches the label and applies the data field 204a to the text. Additionally or alternatively, the medical data application 126 may cause processor 150 to determine a location for data field 204a based on a location of data field 202.

The above-described embodiments use the portable device 104 as a keyboard emulator that transmits keyboard inputs to computer 106. As such, the medical data application 126 may include an on-screen keyboard feature or use an on-screen keyboard of portable device 104. A clinician may use the keyboard to manually enter medical information at computer 106. The manual entry may be performed when extracted text does not match text depicted within in image. The manual entry may also be performed to supplement medical information within an image to provide, for example, labels, context, notes, annotations, etc.

In other examples, the portable device 104 may additionally emulate another peripheral input device, such as a mouse. Here, the medical data application 126 causes processor 150 to transmit one or more message to computer 106 additionally or alternatively designating portable device 104 as a mouse input device. After a connection with computer 106 is established, a clinician may move a cursor on portable device 104, which causes the medical data application 126 to operate with processor 150 to track the movement. The medical data application 126 then causes processor 150 to send one or more message indicative of the movement to computer 106, which moves cursor 212 accordingly. Such a configuration enables a clinician at portable device 104 to select a document, file, and/or template at computer 206 and/or select a location in a document, file, and/or template on screen 132 of computer 106.

In some embodiments, the medical data application 126 may be configured to provide a remote display of screen 132 of computer 106 at portable device 104. After a connection 134 is established, the medical data application 126 may operate with processor 150 to transmit one or more message specifying that portable device 104 is a display device. The one or more message may cause computer 106 to designate connection 134 as an output endpoint that is to receive video images from a video processor for rendering screen 132 onto screen 128 of portable device 104. The medical data application 126 may also cause portable device 104 to be designated as a keyboard and/or mouse with the computer 106, thereby enabling remote control of computer 106 for entry of selected relevant medical device data.

Figure 4:
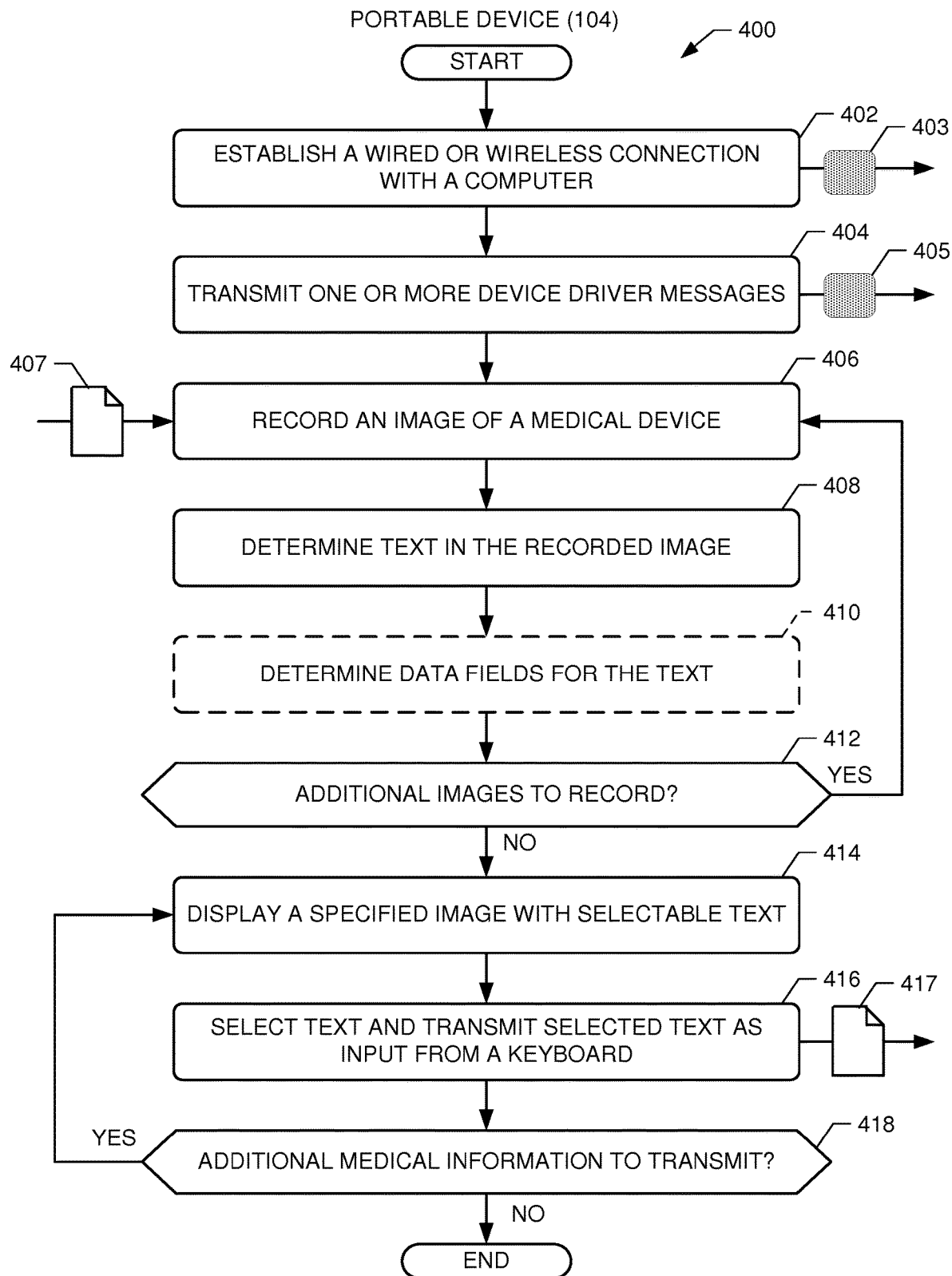
FIG. 4 is a schematic flow diagram illustrating a procedure to transfer medical device data from the portable device to a computer, according to an example embodiment of the present disclosure.

FIG. 4 is a flow diagram of one example procedure 400 for transferring medical information from portable device 104 to computer 106 of FIGS. 1 to 3. Although procedure 400 is described with reference to the flow diagram illustrated in FIG. 4, it should be appreciated that many other methods of performing the steps associated with the procedure 400 may be used. For example, the order of many of the blocks may be changed, certain blocks may be combined with other blocks, and many of the blocks described may be optional. For example, the order of the blocks may be modified based on whether relevant medical information is transmitted after each image is recorded or after all images are recorded. In addition, example procedure 400 may include optional blocks for prompting a user to record an image of a screen 110 and/or identifier 112 of a medical device 102. Further, the actions described in procedure 400 may be performed among multiple devices including, for example portable device 104 and clinician or CIS computer 106.

Example procedure 400 begins in one embodiment when medical data application 126 is launched on portable device 104 and operates with processor 150 to establish a wired and/or wireless connection with computer 106 (block 402). Establishing a connection may include, for example, transmitting and/or receiving one or more message 403 providing a device address, network address, and/or protocol information. In an example, connection establishment may include a Bluetooth® pairing process or Wi-Fi connection initiation. The example portable device 104 then transmits one or more device driver message 405 to computer 106 (block 404). The one or more device driver message 405 specifies and/or designates portable device 104 as an input device. For example, the one or more device driver message 405 may provide a driver file for installation at computer 106. In some instances, the operations described in connection with block 404 may be omitted if the portable device 104 has already installed a driver file on computer 106. In other instances, the operations described in connection with block 404 and/or block 402 may be performed after steps 406 to 412, after the images have been recorded and medical information is available to be transmitted.

In block 406, example portable device 104 records an image 407 of a medical device 102a to 102c, consumable 120, patient 122, etc. The image may include an identifier 120, and/or a screen 110 of the medical device 102a to 102c. Portable device 104 then determines or identifies text within the recorded image (block 408). For example, the portable device 104 may perform an OCR routine on the image. In instances in which the image includes a barcode and/or a QR code, portable device 104 decodes the barcode and/or QR code. In any case, the imaged or coded data is converted into textural or American Standard Code for Information Interchange ("ASCII") characters. In some embodiments, portable device 104 may also determine data fields for the identified text (block 410). The data fields may be determined using, for example, a data template. As described above in connection with FIGS. 2 and 3, the data template may specify locations of certain text and/or specify labels of certain text used for placing data fields on identified text within the recorded image. In some instances, the data fields and/or data template may be selected by a clinician and/or determined from an identifier 112 of the medical device 102. Alternatively, instead of using templates, procedure 400 may instead prompt clinician that the recently recorded image has relevant medical information for extraction, selection, and/or transfer.

Example procedure 400 continues in one embodiment by determining if there are additional images to record (decision block 412). In an example, procedure 400 may include a list of images needed to be recorded for a specified therapy or medical procedure. The procedure, via the portable device 104 may guide a clinician through a sequence to obtain all needed images or provide prompts to obtain images containing medical information that has been determined to be needed and missing. In other instances, the clinician may determine which images are needed. In any case, if additional images are to be recorded, the procedure 400 returns to block 406.

If no additional images are needed, as determined at decision block 412, a clinician begins the process to transfer relevant medical information from portable device 104 to computer 106. The process in the illustrated embodiment includes enabling the clinician to select an image from which relevant medical information is to be transferred. The selection of the image causes the portable device 104 to display the image on screen 128 (block 414). It should be appreciated that the selected image includes identified text, and optionally data fields. The clinician may also specify at computer 106, using cursor 212, a location in a document, file, and/or template into which the relevant medical information is to be entered. Portable device 104 then receives a selection of the relevant medical information and/or data fields with relevant medical information for transmission. Selection may be performed by the clinician pressing on the area of the touch screen 128 of portable device 104 corresponding to the medical information to be transmitted to computer 106 as a keyboard input. Selection of the relevant medical information and/or data fields causes the portable device 104 in an embodiment to automatically transmit the corresponding text to computer 106 (block 416). The text of the relevant medical information and/or text corresponding to selected data fields of an image is included in at least one message 417, as shown in FIG. 4. The text may be provided sequentially and/or in a string, such that it is received at computer 106 as though it is being entered from a keyboard.

After the selected text has been transmitted to computer 106, the portable device 104 determines if additional relevant medical information is to be transmitted (decision block 418). In some examples, the portable device 104 operates a sequence routine that provides prompts for a clinician to select the appropriate text and/or images for transfer. The routine may be matched with an order of data entry presented by the clinician's software. If so, the cursor 212 on the clinician's software may be configured to auto-advance to the next data entry field so that the clinician does not have to manipulate the cursor. In any case, the routine of portable device 104 and the order of data entry on computer 106 may be matched to streamline the keyboard data transfer. In other examples, the clinician may know which relevant medical information is needed next for transmission according to clinician software on computer 106. If there is additional relevant medical information, as determined at decision block 418, procedure 400 returns to blocks 414 and 416, where the clinician specifies the image and/or relevant medical information for keyboard transmission. If there is no additional relevant medical information for transmission, as determined at decision block 418, the example procedure ends 400.

It should be appreciated that in some examples, the clinician may select relevant medical information for keyboard transfer before a connection with computer 106 exists. Here, portable device 104 queues the medical information until a connection is established. In some instances, once the connection is established, portable device 104 sends the queued medical information serially to computer 106 without intervention from a clinician. In other instances, a clinician selects which of the queued data is to be transmitted so as to be able to specify entry locations in a document, file, and/or template of the clinician's software using cursor 212 on computer 106, as has been described herein.

IV. Additional Clinician Environment Embodiment

Figure 5:
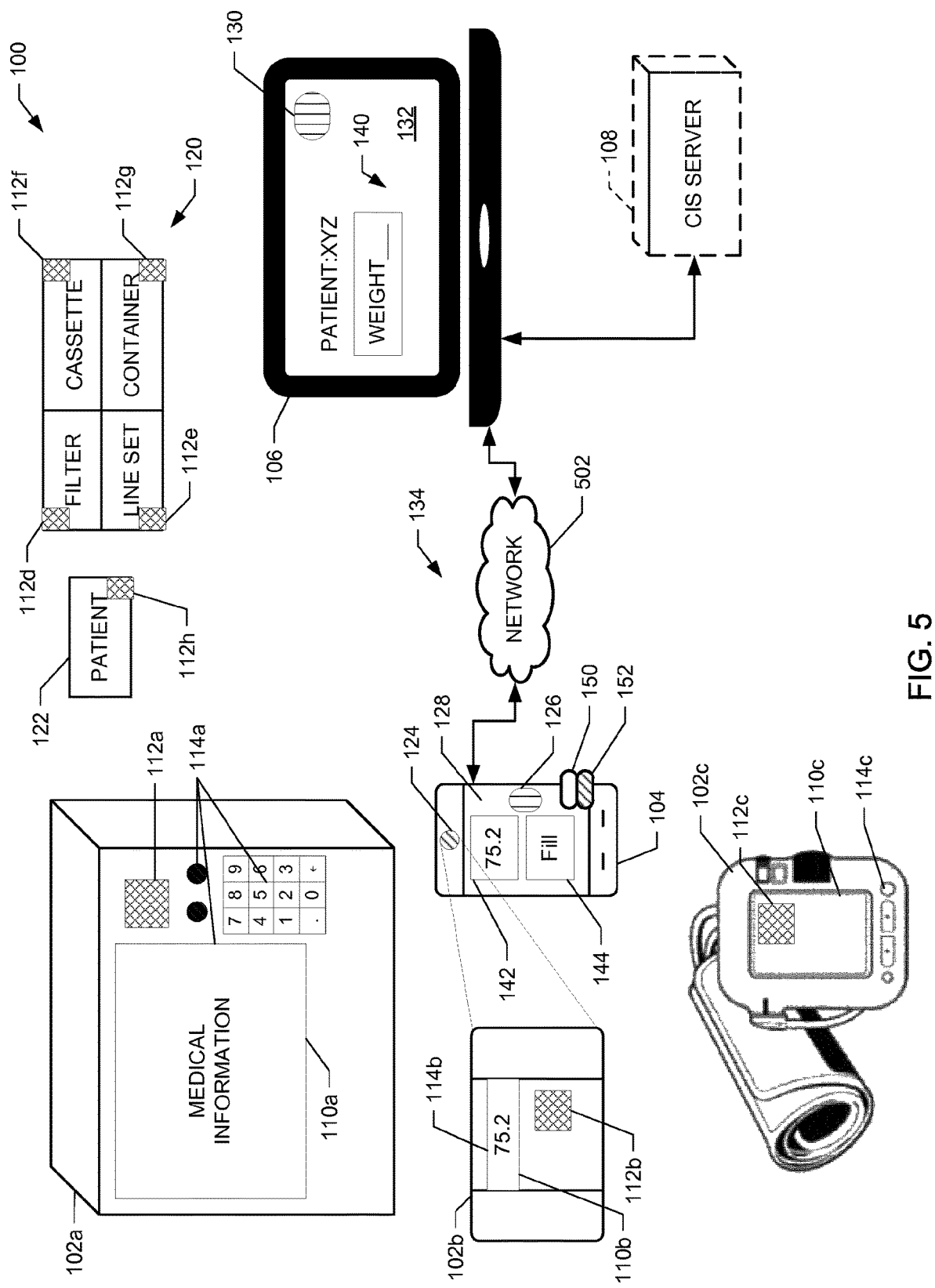
FIG. 5 is a schematic diagram illustrating a clinical system including a clinician computer and a portable device connected via a network, according to an example embodiment of the present disclosure.

FIG. 5 shows an alternative embodiment in which connection 134 is provided over a network 502. In the example of FIG. 5, the network 502 may include a LAN, a wireless LAN, a wide area network, such as the Internet, and/or Wi-Fi. In some instances, portable device 104 uses the medical data application 126, operating with processor 150, to establish a secure network connection (e.g., a virtual private network ("VPN")) across network 502 for conveying medical information. Such a configuration enables portable device 104 to populate a patient medical template over remote distances and/or from a remote location. For instance, computer 106 may be located at a centralized medical system while portable device 104 is located at a clinic. The portable device 104 transmits (e.g., transmits securely) the medical information over the network 502 for completing a template.

In some embodiments, computer 106 may be operated in a cloud computing or distributed computing environment. In other words, the patient medical template may be stored and populated offsite at a location with relatively more processing and/or memory capability. Such a configuration enables portable device 104 to access computer 106 from anywhere in the world to complete patient medical templates. Further, the offloading of processing and memory to computer 106 enables portable device 104 to operate as a thin client or keyboard to remotely complete patient medical templates.

V. Embodiments with a Template Application

In the examples described in connection with FIGS. 1 to 4, computer 106 does not require specialized applications or software to provide for data entry. FIG. 5 shows an embodiment in which computer 106 may include or otherwise operate a template application 130 configured to manage the population and/or completion of patient medical templates. It should be appreciated that the use of the template application 130 is not limited to embodiments with the network 502 and may be integrated with the examples of FIGS. 1 to 4. In some embodiments, the template application 130 may be provided on computer 106 when local connection 134 is made with the portable device 104.

In the illustrated example of FIG. 5, medical data application 126 of the portable device 104 is configured to operate in cooperation with the template application 130 of computer 106 to populate one or more patient medical template. In the illustrated embodiment, screen 132 of computer 106 displays a patient medical template 140. In other examples, template 140 is not displayed before, during, and/or after population. Instead, template application 130 may open a session for populating patient medical template 140, which may be stored as a file in a write-accessible portion of a memory.

Example template 140 has a data field for patient weight. To obtain the patient weight, template application 130, in one embodiment, causes instructions to be sent to medical data application 126 regarding the recording of images from a weight scale. The instructions may include, for example, text for a message to be displayed by medical data application 126 on screen 128 of portable device 104, such as a prompt for a clinician to record an image of a patient weight. The clinician uses camera 124 of portable device 104 to record an image of screen 110*b* of weight scale medical device 102*b* after a patient weight measurement is measured. The image is shown on screen 128 of portable device 104 as image 142, which in the example shows medical information of "75.2".

The medical data application 126 analyzes or otherwise extracts medical information text from image 142 using, for example, OCR. The medical data application 126 prompts the clinician to verify that the extracted medical information matches the data in the image 142. The clinician provides verification by selecting a verify icon 144, which causes medical data application 126 to transmit the medical information to computer 106. The template application 130 populates the weight field of patient medical template 140 with the received medical information. Accordingly, medical data application 126 operates with processor 150 to cause the portable device 104 to operate as a remote keyboard for computer 106 to complete data fields of template 140. The following description provides additional disclosure regarding how medical information is populated into one or more patient medical templates.

VI. Patient Medical Template Embodiments

Figure 6:
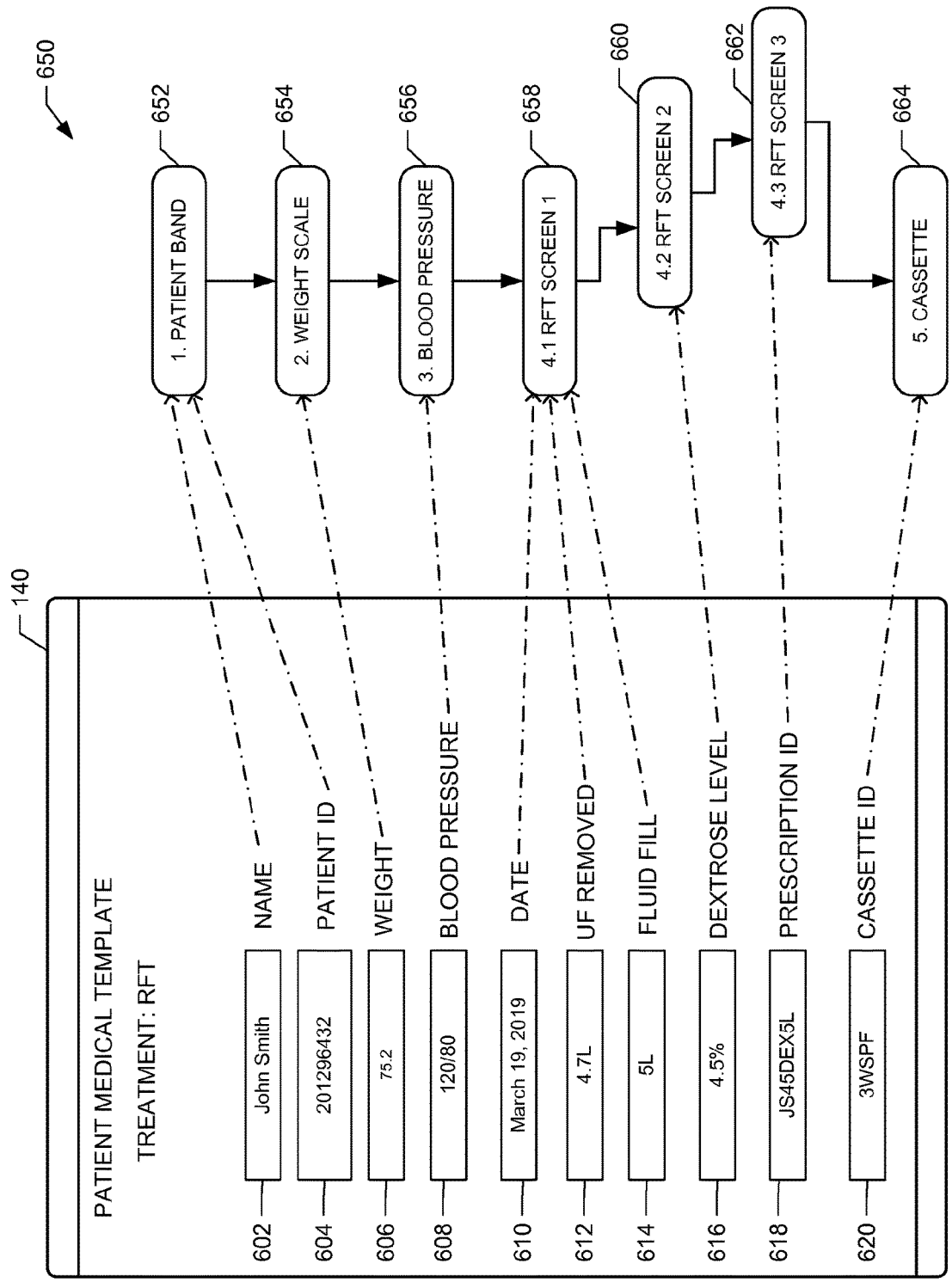
FIG. 6 is a schematic diagram illustrating an example patient medical template used in the clinician system of FIGS. 1 and 2 for storing medical device data, according to an example embodiment of the present disclosure.

FIG. 6 is a schematic diagram of an example patient medical template (e.g., template 140 of FIGS. 1 and 2), according to an example embodiment of the present disclosure. The example patient medical template 140 is configured for a renal failure therapy and includes relevant data fields 602, 604, 606, 608, 610, 612, 614, 616, 618, and 620. The example data fields include a field 602 for a patient's name, a field 604 for a patient identifier, a field 606 for a patient's weight, a field 608 for a patient's blood pressure, a field 610 for a date of treatment, a field 612 for an amount of UF removed, a field 614 for an amount of total fluid provided to a patient, a field 616 for a dextrose level, a field 618 for a treatment prescription identifier, and a field 620 for a disposable cassette identifier.

The example data fields of the patient medical template 140 may be populated from one or more different medical information including, device information, patient information, and/or consumable items. For example, the patient name field 602 and patient identifier field 604 may be populated from image(s) recorded by portable device 104 of the identifier 122*h* of the patient 122 of FIGS. 1 and 2. The blood pressure field 608 may be populated from an image recorded by portable device 104 of screen 110*c* of the blood pressure medical device 102*c*, while weight field 606 may be populated from an image recorded by the portable device 104 of screen 110*b* of weight scale medical device 102*b*. The date field 610, the UF removed field 612 and the fluid fill field 614 may be populated from an image recorded by portable device 104 of screen 110*a* (showing a treatment status window) of the renal failure therapy medical device 102*a*. Similarly, the dextrose level field 616 may be populated from an image recorded by portable device 104 of screen 110*a* (showing a setup window) of the renal failure therapy medical device 102*a*, while prescription identifier field 618 may be populated from an image recorded by portable device 104 of screen 110*a* (showing a prescription window) of the renal failure therapy medical device 102*a*. Finally, the cassette identifier field 620 may be populated from an image recorded by portable device 104 of identifier 112*f* of the disposable cassette consumable item 120.

It should be appreciated that in other embodiments, the patient medical template 140 may include additional or fewer fields. For example, template 140 may additionally include data fields for pre-treatment patient weight and post-treatment patient weight, patient glucose level, and/or patient birth date. In another example, template 140 may include fields for a fill rate, a dwell time, a drain or fluid removal rate, a blood flow rate, an effluent dose, an ultrafiltration removal rate, a dialysis solution removal rate, a total dialysis solution infused, dialysis solution flow, replacement pre-flow, replacement post-flow, patient weight balance, return pressure, excess patient fluid sign, filtration fraction, a time remaining, dialysis solution concentration, dialysis solution name, a patient identifier, a room identifier, a care area identifier, a timestamp when the data was generated, an alarm condition, an alert condition, and/or an event. In other examples, template 140 may contain fewer fields, such as omitting data fields 614 to 620. The amount and types of data fields included within patient medical template 140 may be selected by medical administrators based on medical information needed to adequately document a treatment for a patient's EMR.

The patient medical template 140 illustrated in FIG. 6 is configured to be stored on clinician or CIS computer 106 of FIGS. 1 and 2. Upon receiving a request to populate a template for a patient, computer 106 makes a copy or creates an instance of template 140. Medical information received from portable device 104 is inputted by computer 106 into the appropriate data fields 602 to 620 of the copy or instance of the template 140. Once complete, the copy or instance is stored in an EMR repository as a medical record of the patient.

Example computer 106 may store different types of patient medical templates for different treatments, patient physiological conditions, and/or different medical devices. In an example, computer 106 may store separate patient medical templates for a hemodialysis treatment, a peritoneal dialysis treatment, an infusion treatment, etc. Further, for each type of treatment, computer 106 may store different patient medical templates based, for example, on a type of hemodialysis medical device connected to a patient for treatment. Additionally or alternatively, computer 106 may store different patient medical templates for patient medical conditions, such as blood sugar monitoring, fluid balance monitoring, or templates for a general overall health assessment.

A clinician may select a patient medical template using, for example, portable device 104 and/or computer 106. For instance, upon beginning a session to populate a template, a clinician may select a treatment type, causing computer 106 to create a copy or instance of the corresponding template. Alternatively, computer 106 may select a patient medical template based on an identifier of a medical device, a patient, and/or a consumable item received from portable device 104.

The example patient medical template 140 is configured to include or operate in cooperation with a routine 650 that coordinates the population of the data fields 602 to 620. In some embodiments, routine 650 may be programmed as metadata for the respective data fields 602 to 620. In other examples, routine 650 may be stored in computer 106 in relation to the patient medical template 140. Further, in these other examples, selection of template 140 causes routine 650 to be executed. The example routine 650 contains modules 652 to 664 that provide associations between data fields 602 to 620 and corresponding medical devices 102, patient identifier 112*h*, and/or consumable items 120.

The patient band module 652 may include metadata or preformatted messages instructing a clinician or patient to record an image of a patient's wristband. The patient band module 652 may also include character verification checks to ensure the received medical information conforms to text requirements for a patient's name and patient identifier. For example, patient band module 652 may reject or discard medical information for a patient's name that includes numbers.

The weight scale module 654 may include metadata or preformatted messages instructing a clinician or patient to record an image of identifier 112*b* and screen 114*b*. The weight scale module 654 may also include character verification checks to ensure the received medical information is within an acceptable range of values or of the correct unit type. In some instances, weight scale module 654 may use medical information from the identifier 112b to confirm that the medical information from screen 114b is patient weight medical information. In other instances, medical information from identifier 112b is used for selecting a data template based, for example, on a model or type of the weight scale. The data template is used by portable device 104 and/or computer 106 to identify relevant weight scale medical information that was extracted from images of screen 114b, and is discussed in more detail in connection with FIG. 7.

The blood pressure module 656 is similar to weight scale module 654 with respect to the blood pressure medical device 102c. The renal failure therapy ("RFT") modules 658 to 662 are also similar to weight scale module 654. However, multiple modules 658 to 662 are used for the renal failure therapy machine 102a for each of the different windows from which medical information is needed. For example, module 658 provides messages for acquiring images of the identifier 112a and a first window showing a treatment status window, while module 660 provides one or more message for acquiring an image of a setup window and the module 662 provides one or more message for acquiring an image of a prescription window of the renal failure therapy medical device 102a.

The cassette module 664 may include metadata or preformatted messages instructing a clinician or patient to record an image of identifier 112f and disposable cassette consumable item 120 and/or a label on packaging or the cassette consumable itself. It should be appreciated that routine 650 may include additional modules if the patient medical template 140 includes additional data fields.

The example routine 650, and more specifically, modules 652 to 664 are executable, in the illustrated embodiment, by template application 130 of FIGS. 1 and 2. Each of modules 652 to 664 may include metadata and/or instructions for a clinician to obtain medical information for populating the related data fields. The template application 130 may progress sequentially through routine 650 to accordingly provide a step-by-step process for remotely completing patient medical template 140. In some instances, template application 130 may not progress to the next module until the medical information is received for the current module. In some instances, template application 130 may cause periodic messages to be transmitted to portable device 104 until the appropriate medical information for the current module is received.

In other instances, routine 650 may react to inputs received from the portable device 104. For example, portable device 104 may provide a message indicating that identifier 112b of weight scale medical device 102b has been recorded first. The template application 130 executes weight scale module 654 and identifies a request message to send to portable device 104. The template application 130 then waits for medical information from weight scale medical device 102b to be transmitted to computer 106. Once the medical information is received, the template application 130 uses data verification checks in the module 654 to ensure the data is within an acceptable range, formatted correctly, and/or in the appropriate units. In some instances, module 654 may include conversion or formatting instructions, which are used by template application 130 to prepare the medical information for inclusion in weight field 606. Once the data is in the appropriate format and unit, template application 130 writes the medical information to weight field 606.

In alternative embodiments, patent medical template 140 may not have an associated routine 650. Instead, template application 130 is configured to read data fields 602 to 620 of patient medical template 140 to determine, for example, incomplete data fields. In these alternative embodiments, template application 130 identifies missing data and transmits one or more message to portable device 104, prompting a clinician for the missing data.

Further, to populate the data fields, template application 130 may read a name of data field 602 to 620 (and any corresponding metadata) to create and send a message to a clinician prompting the recording of certain images. In an example, weight data field 606 includes metadata identifying a weight scale as the related medical device 102. The template application 130 determines that data field 606 is unfilled, reads the corresponding metadata, and constructs a message instructing a clinician to record an image of a screen of a weight scale. In the illustrated embodiments, template application 130 may progress sequentially through template 140 searching for unfilled data fields and accordingly requests medical information from a clinician via portable device 104. Alternatively, template application 130 may progress through template 140 according to a predetermined order or sequence. For example, template application 130 may search first for data fields associated with a patient wristband, followed by data fields for a weight scale medical device, data fields for blood pressure medical device, and data fields for a renal failure therapy medical device.

VII. Data Template Embodiments

Figure 7:
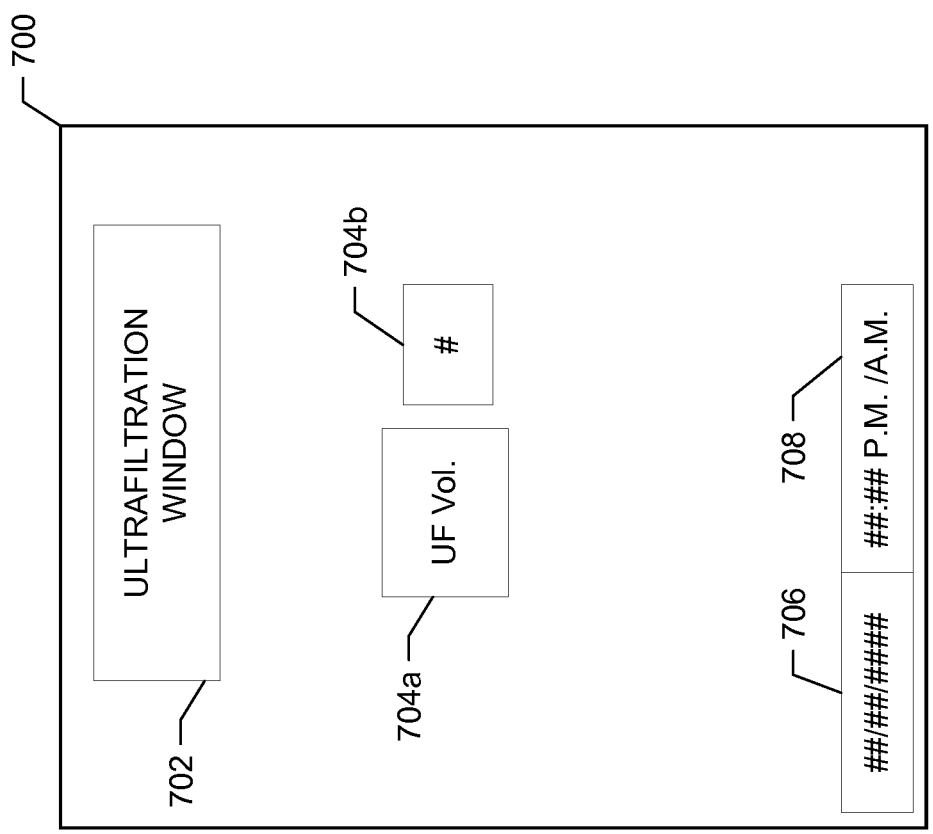
FIG. 7 is a schematic diagram illustrating a data template used in the clinician system of FIGS. 1 and 2 for identifying medical device data extracted from one or more image, according to an example embodiment of the present disclosure.

FIG. 7 illustrates a schematic diagram of a data template 700, according to an example embodiment of the present disclosure. The example data template 700 is used by the medical data application 126 and/or the template application 130 to identify extracted data as being relevant medical information. Generally, screens 110 of medical devices 102 show medical information. Some of the data is relevant for inclusion in patient medical template 140. Other of the data may be less relevant or not relevant. Further, depending on a model of medical device, the medical information may be in different locations or have different labels. Data template 700 is configured to specify locations and names of relevant medical information.

The example data template 700 is stored, for example, at clinical computer 106 of FIGS. 1 and 2. The data template 700 is stored with a plurality of other data templates for different types and/or models of medical devices 102 and/or consumable items 120. Upon receiving an identifier 112 of a medical device 102 (or specification of a medical device by a clinician), computer 106 selects and transmits (a copy of) corresponding data template 700 to portable device 104. In other examples, data template 700 is stored at portable device 104 and selected by medical data application 126 based upon an identifier 112 recorded in an image. Additionally or alternatively, medical data application 126 and/or the computer 106 may use image processing to select a data template that best matches a recorded image.

The example data template 700 of FIG. 7 includes device data (or text) fields 702, 704, 706, and 708 that specify where certain medical information is located on a particular window of a medical device. In some examples, data template 700 is graphical such that an image analysis is performed to align fields 702 to 708 with extracted text in an image. In other examples, data template 700 includes a file (or other data structure) having coordinates or positions for each of device data fields 702 to 708 relative to an origin. The medical data application 126 may identify an origin in the image with the extracted text and identifies text for each of data fields 702 to 708 based on substantial matches to locations in data template 700. In some examples, medical data application 126 may scale the image to match a size or coordinate space of data template 700.

Each of the illustrated data fields 702 to 708 includes label text in addition to coordinates and/or locations. For example, device data field 702 includes label text "Ultrafiltration Window", while device data field 704*a* includes label text "UF Vol.". The medical data application 126 matches the label text to similar text extracted from an image. In some instances, matches between label text are used exclusively for identifying device data fields, rather than using positional or image analysis.

Matches between the label text, including label text for non-relevant device data fields, may be used to confirm that the image is from the correct window or screen of a medical device. For example, medical data application 126 may match label text "Ultrafiltration Window" to corresponding extracted text in relatively the same location of a recorded image. The match confirms that the image has been recorded from an ultrafiltration window of a renal failure therapy medical device 102*a*. However, the extracted text is not relevant medical information for patient medical template 140. If the label text does not match the extracted text, medical data application 126 may display a message prompting the clinician to record an image of the Ultrafiltration Window of renal failure therapy medical device 102*a*.

The label text associated with device data fields 706 and 708 may be used to confirm a recorded image is current, or recorded within a determined time period. For example, some windows of medical devices display a current date and time. This information may be extracted by medical data application 126 and identified using device data fields 706 and 708. The medical data application 126 then compares the extracted date/time to a current date/time rules or limits associated with the device data fields 706 to 708 to determine whether the recorded image is current. For example, medical data application 126 may determine another image is required to be recorded if the date does not match or the time is not within a predetermined threshold (e.g., five minutes, 15 minutes, 60 minutes, 3 hours, etc.) of a current time on portable device 104.

The example device data fields 704*a* and 704*b* are used by medical data application 126 to identify relevant medical information. In some instances, device data fields 704*a* and 704*b* include a flag or metadata indicative that the corresponding data is relevant. By comparison, device data fields 702, 706, and 708 may include a flag or metadata indicative that the corresponding extracted data is not relevant for patient medical template 140. In the example illustrated in FIG. 7, medical data application 126 uses the label text of data field 704*a* to locate corresponding extracted text. The medical data application 126 then uses a positional relationship between device data fields 704*a* and 704*b* or text value markers to identify extracted medical information that corresponds to the numerical value of the ultrafiltration volume. The medical data application 126 copies the extracted medical information related to field 704*b* to populate, for example, data field 612 of patient medical template 140. Accordingly, data template 700 enables portable device 104 to operate as a remote keyboard for writing extracted medical information to a patient medical template 140.

VIII. Clinician or CIS Computer Embodiment

Figure 8:
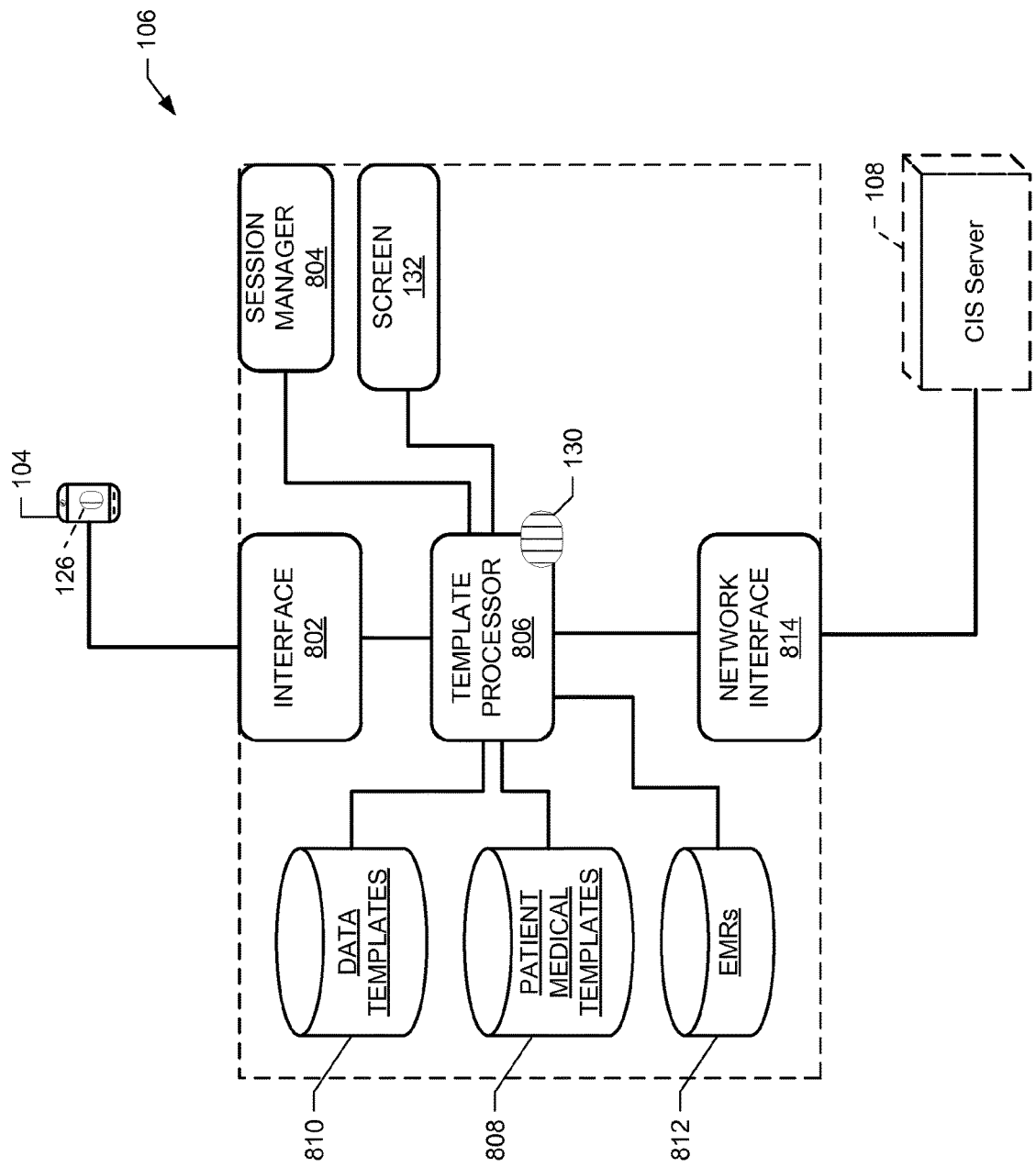
FIG. 8 is a schematic diagram illustrating the clinician computer of FIGS. 1 and 2, according to an example embodiment of the present disclosure.

FIG. 8 is a schematic diagram of clinician or CIS computer 106 of FIGS. 1 and 2, according to an example embodiment of the present disclosure. It should be appreciated that the illustration of computer 106 is exemplary and that some of the blocks may be combined, further partitioned, or removed. In addition, in some embodiments, computer 106 may include additional blocks, such as a block for a user interface.

The example computer 106 includes an interface 802 that provides connectivity with portable device 104. The interface 802 may include, for example a universal serial bus ("USB") port and related software for receiving messages via a USB connection. In other instances, interface 802 may include a Bluetooth® transceiver and related software. The interface 802 is configured, in one embodiment, to receive and convert messages from portable device 104 into a format compatible for internal processing. The example interface 802 is also configured to format or convert messages for transmission to portable device 104. In some instances, interface 802 may encrypt messages for transmission and/or decrypt received messages.

The example computer 106 includes a session manager 804 configured to manage sessions with one or more portable device 104. A session is created for each patient medical template 140 that is requested to be populated. To open a session a clinician at portable device 104 may use medical data application 126 to transmit a request to populate a patient medical template. A session may also be requested by a clinician at computer 106. The request may include an identification of a treatment type. In response, session manager 804 may initiate a session and create a copy of a patient medical template 140 associated with the specified treatment. The session may include storage of a copy of a patient medical template 140 to volatile memory to enable writing to associated data fields. A template processor 806, operating template application 130, maintains the session, in one embodiment, such that messages transmitted through the session are used for writing medical information to the corresponding patient medical template 140.

The computer 106 of FIG. 8 provides screen 132 to display information related to a session, including, for example, a graphical representation of a patient medical template 140. In some instances, screen 132 may display a real-time view of a patient medical template 140 as data fields are being written from portable device 104. A clinician at computer 106 may also request to view a patient medical template 140 during or after completion of the template. The clinician may use screen 132 to verify, for example, that data fields have been populated correctly or to review a patient's medical information generally. In some instances, a clinician may use screen 132 in cooperation with a user interface to modify or add medical information to a data field of template 140.

Example template processor 806 is configured to manage the writing or population of medical information from portable device 104 to a patient medical template 140. For example, upon request from a clinician, template processor 806 selects a template from a patient medical template database 808. Template processor 806 then operates with session manager 804 to create a session for the selected template 140.

During the session, template processor 806 identifies messages from modules of a routine (e.g., the routine 650) for transmission to portable device 104. In some instances, the messages may be transmitted in a predetermined sequence to direct a clinician or a patient through a process to populate a patient medical template. For example, template processor 806 may read module 652 of routine 650 of FIG. 6 and determine a message is to be transmitted that prompts a clinician to record an image of identifier 112h of a patient wristband. Template processor 806 may be configured to wait until medical information related to the identifier 112h is received (for populating the data fields 602 and 604 of FIG. 6) before identifying messages from module 654 that are to be transmitted. In other instances, template processor 806 selects messages based on messages received from portable device 104. For example, processor 806 may receive medical information associated with identifier 112b of weight scale medical device 102b. In response to the received medical information, template processor 806 may determine that module 654 corresponds to the received data and accordingly selects messages prompting an operator to record an image of screen 114b of weight scale medical device 102b.

In addition to sending messages, template processor 806 may be configured to select data templates 700 for transmission to portable device 104. The data templates 700 are stored in a data template database 810 in the illustrated embodiment. The template processor 806 selects data templates 700 based on a type or model of a medical device, which is indicated in medical information corresponding to identifier 112. In some instances, a clinician may specify the model and/or type of medical device type to template processor 806 via a message. Further, when computer 106 is configured to handle more processing, template processor 806 may receive image(s) from portable device 104, extract text from the images, and select the appropriate data template 700 for identifying relevant medical information from the image(s).

In some embodiments, template processor 806 may receive a stream of messages from portable device 104 containing substantially all the medical information for the patient medical template 140. In these embodiments, template processor 806 reads labels, metadata, and/or device data field information provided with the data to determine a data field of template 140 to which the data is to be populated or written. Template processor 806, for example, matches metadata or information of the modules (or data fields 602 to 620 themselves) to the labels, metadata, and/or device data field information provided with the medical information to determine the appropriate data field of template 140.

After populating or otherwise completing a patient medical template, template processor 806 of FIG. 8 is configured to store the completed template to an EMR database 812. The completed template may comprise a patient EMR that provides documentation of the provided treatment. CIS server 108 may access the EMRs at database 812 to enable remote clinicians review the medical information for a patient.

In some embodiments, template processor 806 is configured to periodically transmit the EMRs to CIS server 108 using, for example, a network interface 814 (e.g., an Ethernet port and related software). The network interface 814 may encrypt the EMRs for safe transmission across an open network. Template processor 806 may also receive new data templates and/or patient medical templates from CIS server 108, which are stored to the appropriate databases 808 and 810.

The example patient medical template database 808 stores a plurality of medical device templates for different treatments, models of medical devices, and/or patient conditions. The data template database 810 stores a plurality of data templates for different medical devices and/or different models of medical devices. The EMR database 812 is configured to store a plurality of completed patient medical templates 140 as patient EMRs. Databases 808, 810, and 812 may include any type of computer-readable medium comprising RAM, ROM, flash memory, magnetic or optical disks, optical memory, or other storage media.

IX. Portable Device Embodiment

Figure 9:
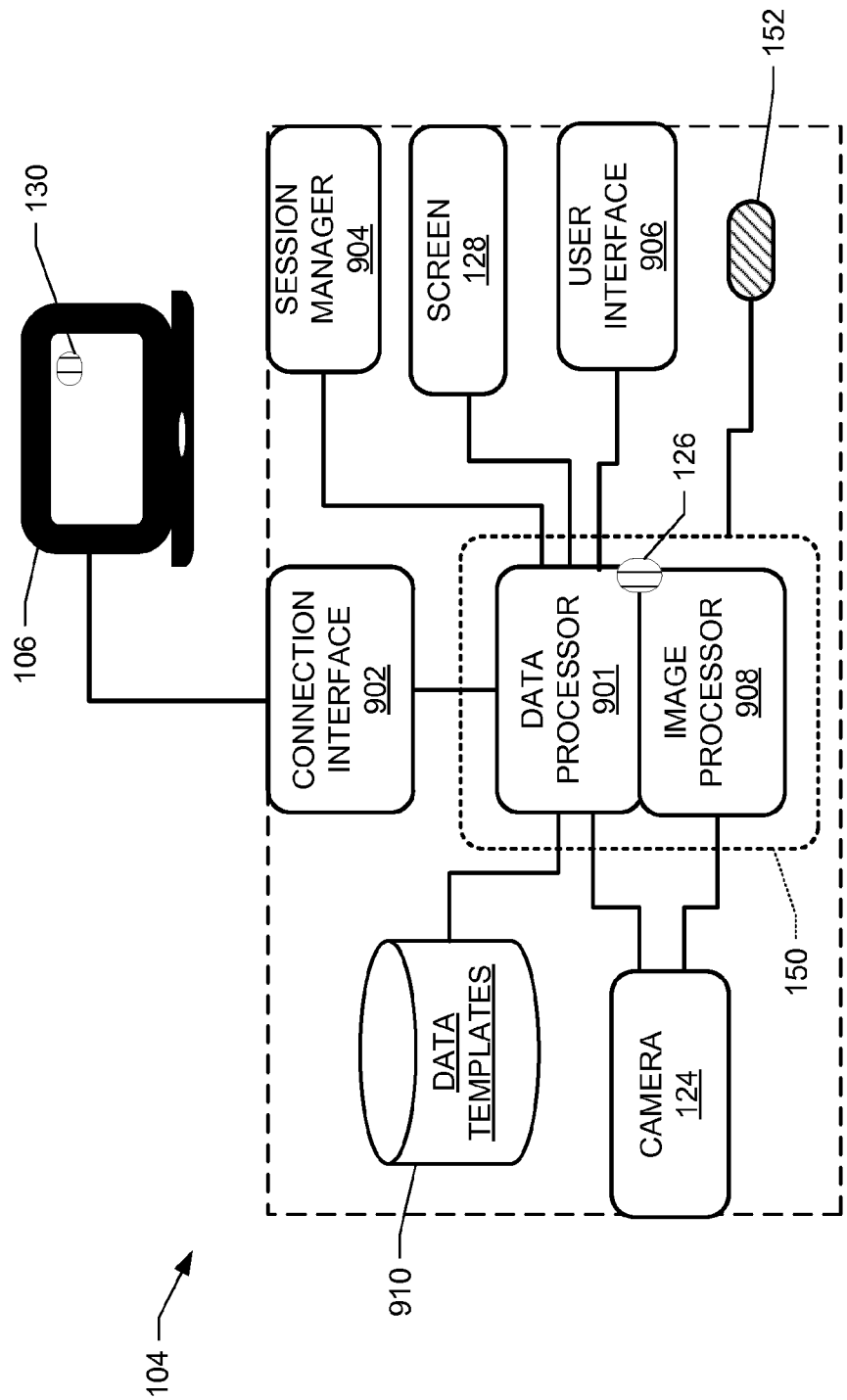
FIG. 9 is a schematic diagram illustrating the portable device of FIGS. 1 and 2, according to an example embodiment of the present disclosure.

FIG. 9 is a schematic diagram of portable device 104 of FIGS. 1 and 2, according to an example embodiment of the present disclosure. It should be appreciated that the illustration of portable device 104 is exemplary and that some of the blocks may be combined, further partitioned, or removed. In addition, in some embodiments, portable device 104 may include additional blocks, such as memory 152 (e.g., memory 152 of FIGS. 1 and 5) storing instructions, which when executed by a data processor 901 (or more generally, processor 150), cause the medical data application 126 to be operated.

The example portable device 104 includes a connection interface 902 for connectivity with the clinician or CIS computer 106. The connection interface 902 may include, for example, a USB port and related software for receiving and/or transmitting messages via a USB connection. In other instances, connection interface 902 may include a Bluetooth® transceiver and related software. The connection interface 902 is configured, in the illustrated embodiment, to receive and convert messages from computer 106 into a format compatible for internal processing. The example connection interface 902 is also configured to format or convert messages for transmission to computer 106. In some instances, connection interface 902 may encrypt messages for secure transmission and/or decrypt received messages.

In some instances, connection interface 902 is configured to convert or otherwise provide medical information to conform to a Health-Level-7 ("HL7") standard. This conversion enables medical information which may, or may not, be provided as HL7 on a medical device 102 to be recorded in an image (losing the HL7 compatibility) and re-formatted into HL7 before being electronically transmitted by portable device 104 to computer 106. In other words, portable device 104 may operate as a network conduit to seamlessly propagate relevant medical information from a medical device to a patient medical template when gaps in network or device connectivity exist.

The example connection interface 902 is configured to transmit one or more device driver messages to computer 106 to establish or configure portable device 104 as a keyboard or other peripheral device. The messages may, for example, configure a USB and/or wireless (e.g., Bluetooth®) endpoint at computer 106. The messages instruct an operating system of the computer 106 to recognize and/or configure the endpoint as a peripheral input. In response to the configuration, the computer 106 may periodically poll the endpoint for text and/or configure interrupts for triggering upon reception of text at the endpoint.

The example portable device 104 of FIG. 9 includes a session manager 904 configured to manage sessions with one or more computer 106. As discussed above in connection with FIG. 8, a session is created for each patient medical template 140 that is requested to be populated. The session manager 904 of portable device 104 receives a request from user interface 114 indicative of a clinician's desire to populate a medical device template. The request may include, for example, a selection of a medical treatment or type of medical device administering a treatment. The session manager 904 transmits a request message to session manager 804 of computer 106 to open a session between devices 104 and 106. During the session, relevant medical information identified at portable device 104 is written to data fields of a patient medical device template 104 at computer 106.

The session manager 904 may open a secure network connection with session manager 804 for the secure transfer of medical information. Additionally or alternatively, session manager 904 may monitor a status of a connection with computer 106 via the connection interface 902. During periods where a connection exists, session manager 904 permits the transmission of medical information in real-time as it is identified to computer 106 for population in a medical device template 140. During periods where a connection does not exist, session manager 904 may queue the relevant medical information for transmission until a connection is detected.

In some embodiments, session manager 904 may manage separate tabs or windows displayed on screen 128 to enable a clinician or patient to populate concurrently multiple active patient medical device templates. The clinician may bring a particular tab or window to a top of screen 128 to indicate which session is active for analyzing images and transmitting medical information for a particular active template. The session manager 904 is also configured to enable a clinician to select which recorded images are associated with each open session.

The example data processor 901 may be configured to manage the acquisition of medical information from one or more image. Such management includes displaying, via the screen, one or more camera message that provides information prompting a clinician or a patient (e.g., an operator) to record certain images. The data processor 901 may receive information for the messages (or the messages themselves) from template application 130 at computer 106. The data processor 901 may display the messages as they are received from computer 106 or wait until, for example, medical information related to a previous message has been transmitted to computer 106. In some embodiments, data processor 901 may cause screen 128 to display an icon or other graphical indication that one or more message is available for a clinician to open and read.

Alternatively, in instances in which patient medical template 140 and/or the routine 650 are located at portable device 104, data processor 901 may determine which messages are to be displayed. To determine which messages are to be displayed, data processor 901 may use rules, a sequence specified by routine 650, and/or metadata associated with the template 140. For example, data processor 901 may display a sequence of messages to guide a clinician through a process to image certain screens and/or windows of medical devices 102 and/or consumable items 120. Data processor 901 controls the timing or sequence of the messages contingent upon the clinician recording a prompted image or sending requested medical information.

The example data processor 901 of FIG. 9 is configured to display camera messages that identify a medical device 102, window of a medical device 102, and/or an identifier on a medical device 102 that is to be recorded. The data processor 901 may also display navigation messages that specify a window of a medical device for imaging. Moreover, data processor 901 may display reminder messages if an image is not recorded within a predetermined time period (e.g., five minutes). The messages may include text providing instructions and/or identifying the intended target for imaging. The messages may also include instructions regarding how to navigate to a certain window using control interfaces 114. The messages may further include graphical elements, such as an exemplary illustration of a medical device 102, consumable items 120, identifier 112, and/or window for which an image is to be recorded.

It should be appreciated that in some embodiments, data processor 901 does not display messages. Instead, data processor 901 is reactive to images recorded by a clinician to determine relevant medical information. For example, upon receiving an indication that an image is recorded, data processor 901 may prompt a clinician to identify a medical device 102 from which the image has been recorded. The prompt may include a pull-down menu of available or common medical devices. In other examples, data processor 901 may request a clinician to indicate data fields in a template and the corresponding relevant medical information in one or more image.

As mentioned above, portable device 104 may be configured to record images of medical devices 102. The example data processor 901 and an image processor 908 (more generally processor 150) operate the medical data application 126 to acquire images and extract text from the images. In an example, a clinician provides an indication via a user interface 906 (e.g., a touchscreen or button on the portable device 104) to record an image. The clinician actuates user interface 906 when, for example, a camera is focused on a medical device 102 window or identifier 112. The data processor 901 receives the indication and instructs camera 124 to record an image. The recorded image is transmitted from camera 124 to image processor 908. In addition, a copy of the image is displayed by data processor 901 on screen 128.

In some embodiments, data processor 901 may cause a ghost image to appear on screen 128 that is illustrative of an image to be recorded. The ghost image is provided on top of a stream of images provided by camera 124 in a preview mode. The purpose of the ghost image is to provide assistance to a clinician or patient confirming that the image to be recorded contains the desired medical information and is recorded at an appropriate distance. For example, data processor 901 may display a ghost image of a given identifier on a given medical device. The clinician aligns portable device 104 such that a stream of images of identifier 112a is aligned positionally with the ghost image. The clinician may then record the image of identifier 112a. In some instances, data processor 901 uses image analysis to determine deltas between the ghost image and the stream of images. The data processor 901 may determine when the deltas are below a threshold, indicating that the images are aligned. Once the images are substantially aligned, data processor 901 may provide a graphical indication on screen 128 indicative that an image can be recorded.

The data processor 901 may provide a prompt asking the clinician to accept the image. After receiving an indication via user interface 906 of acceptance, image processor 908 may analyze the image to identify or otherwise extract text. In some instances, data processor 901 may not prompt a clinician to accept an image. Instead, a clinician may provide an indication via user interface 906 to delete an image. Until an image is deleted, image processor 908 performs an analysis to identify text.

To identify text, image processor 908 uses, for example, OCR. In addition, image processor 908 may determine a location or position of the text with respect to a center or origin of the image. In some instances, image processor 908 may assign two-dimensional coordinates to each character or group of characters. The positional text information may be stored to an image file of the image as metadata. The image processor 908 may also use a clock of portable device 104 to attach a date/time (corresponding to a time when the image was recorded) to metadata associated with the image.

In addition to performing OCR to identify text, image processor 908 may also be configured to identify patients 122, medical devices 102, and/or consumable items 120 using image analysis. For example, image processor 908 may access a library of patient images to identify a patient within an image. In this example, image processor 908 may use facial recognition routines to determine a match. Such a comparison may be made in lieu of the patient having a wristband with identifier 112h. The image processor 908 may use similar routines and/or algorithms for identifying medical devices 102 and/or consumable items 120.

The example data processor 901 is also configured to decode identifiers 112. Decoding may include correlating positions and thicknesses of lines and/or rectangles into relevant medical information. The coded lines and rectangles may correspond to a sequence of letters and/or numbers. For example, data processor 901 may use the lines or rectangles of the identifier 112 to determine a device model number, medical device type, asset code, etc.

The example image processor 908 of FIG. 9 transmits the images with the extracted or otherwise identified text and/or medical information to data processor 901. The example data processor 901 uses, for example, one or more data templates 700 from a data template database 910 to identify relevant medical information from the extracted text. In some examples, data processor 901 receives data templates 700 from computer 106, which may then be stored in database 910. In other examples, data processor 901 maintains database 910 with data templates 700.

As discussed above in connection with FIG. 7, data processor 901 may use known positional relationships of text in an image and text label(s) to determine which of the extracted text corresponds to relevant medical information. In some embodiments, data processor 901 selects a data template based on an indication of the model or type of medical device 102 and/or consumable item 120. The indication may be determined from a previous image of an identifier 112 and/or received from a clinician via user interface 906. In other examples, data processor 901 compares the data templates in the database 910 to the image with the extracted text to find a match. In these other examples, data processor 901 uses text labels and a position of the text between the image and data templates to determine a match.

Data processor 901 is configured, after identifying relevant medical information, to write or otherwise populate the relevant medical information into one or more data field of patient medical template 140. In an example, the device data fields of data template 700 are used to identify the data fields of template 140 using, for example, name or label matching. In other instances, data processor 901 uses a look-up table (associated with the data template) that correlates the device data fields to certain data fields of template 140. For example, the lookup table may specify that device data field 704b of FIG. 7 corresponds to data field 612 of FIG. 6. Accordingly, data processor 901 writes the extracted relevant medical information related to device data field 704b to the data field 612 of FIG. 6.

The data processor 901 writes the extracted relevant medical information to template 140 by sending one or more write message to template processor 806 of the computer 106. The relevant medical information may be formatted serially in one or more message to emulate text entry from a keyboard at computer 106. The relevant medical information may additionally or alternatively be provided in a message as American Standard Code for Information Interchange ("ASCII") characters in an HL7 format. The message may include a header that specifies a write command and the intended data fields of template 140 to which the medical information is to be written. In some embodiments, the messages may include short message service ("SMS") messages that include ASCII text of the relevant medical information and an indication of the one or more data field to which the data is to be written. In some instances, template 140 may be stored at an address such that messages transmitted from data processor 901 are provided with a destination address of template 140 for data population.

In some embodiments, data processor 901 may prompt a clinical to confirm or approve the relevant medical information before it is sent to computer 106. The prompt may include displaying the relevant medical information to be transmitted with a verify button for the clinician to select using user interface 906. The prompt may also include a copy of the recorded image from which the medical information has been extracted to allow the clinician determine the extracted data matches the imaged data. After receiving a verification indication, data processor 901 transmits the relevant medical information to the template application 130 of computer 106. In some instances, the clinician may use the user interface 906 to modify the medical information before sending to computer 106.

In further embodiments, data processor 901 may perform a check to ensure the extracted data for certain device data fields are within a predetermined range and/or of a specified type. The device data template may include metadata or rules for certain fields. For example, metadata or rules for a weight data field may specify that a predetermined range is between 20 kg and 200 kg. For values outside the predetermined range, data processor 901 may display an error on screen 128 or prompt a clinician to record another image or amend the value.

As mentioned above, in some examples, data processor 901 does not use data templates. Instead a clinician may identify relevant medical information from extracted text in an image. In an example, data processor 901 displays the recorded image with the extracted text. A clinician selects a portion of the text using user interface 906. Data processor 901 may then determine data fields of a patient medical template 140 for the selected relevant medical information using, for example, text labels in proximity to the selected text or an input received from the clinician. Additionally or alternatively, the clinician may select the data fields from a graphical display of template 140.

X. Remote Population of a Patent Medical Template Workflow Example

FIGS. 10 to 20 are schematic diagrams showing example workflows for populating a medical device template 140 using images recorded by the portable device, according to an example embodiment of the present disclosure. The illustrated workflow shows how relevant medical information is obtained from the renal failure therapy medical device 102a and the weight scale medical device 102b for population into a patient medical template 140 at the clinician or CIS computer 106. In other examples, the workflow may include additional medical devices, such as blood pressure medical device 102c, an infusion pump, an oxygen sensor, a respiratory monitor, a glucose meter, an ECG monitor, etc. Further, the workflow may include recording images of patient 122, consumable items 120, and/or identifiers 112d to 112h.

The workflow process begins after portable device 104 transmits a message to computer 106 indicative of a treatment to be documented. Alternatively, the message may indicate that a clinician desires to populate a patient medical template. In some instances, a session is created to populate a template. In other instances, a template is made available by template application 130 at a designated address.

FIG. 10 shows that template application 130 transmits a message 1002 providing a camera message prompting a clinician to record an image of the identifier 112*a*. As discussed above in connection with FIG. 8, message 1002 may be determined from modules in routine 650. Portable device 104 receives message 1002 and displays information 1004 from message 1002 on screen 128. In response to viewing information 1004 from message 1002, the clinician uses camera 124 of portable device 104 to record an image of identifier 112*a*. The medical data application 126 extracts medical data information from the image and transmits a message 1006 to template application 130 with the relevant medical data information.

In FIG. 11, the example template application 130 determines a medical device type and/or model based on medical information in message 1006 of FIG. 10. The template application 130 then determines a data template 700 based on the medical device type and/or model and/or a camera message for the medical device type and/or model. The template application 130 then sends the data template and/or the camera message in message 1102 to portable device 104. The medical data application 126 operates with processor 150 to display camera message information 1104 from the message 1102, prompting the clinician to record an image of screen 110*a* of the medical device 102*a*. The information 1104 also identifies a window of the medical device 102*a*. Accordingly, the clinician records an image of screen 110*a* of the renal failure therapy medical device 102*a* using camera 124 of portable device 104.

Figure 12:
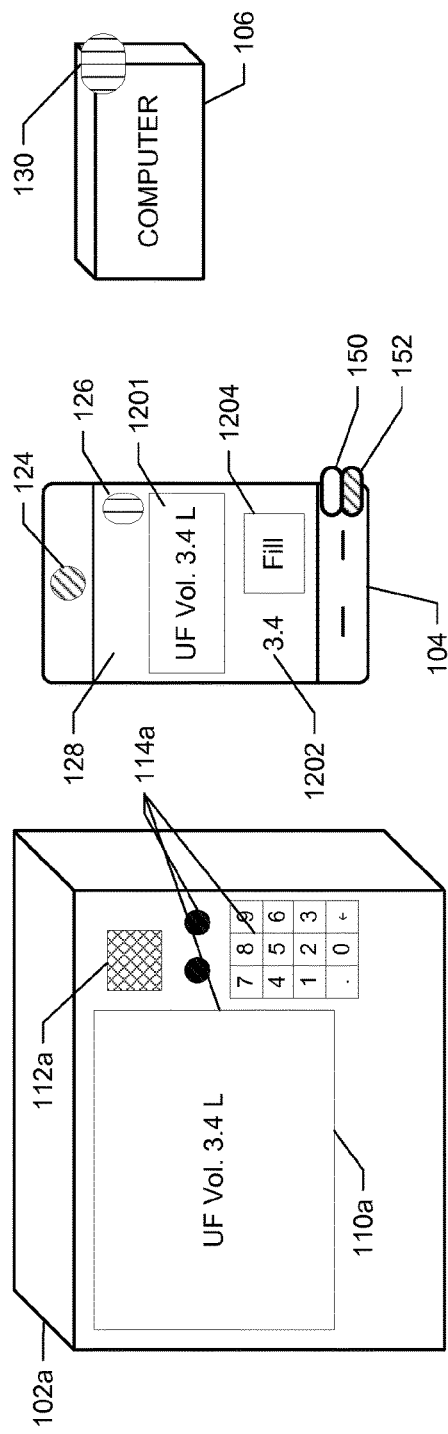

In FIG. 12, the example medical data application 126 causes processor 150 to extract text data from the recorded image (shown as image 1201) and uses the data template from the template application 130 (received in the message 1102) to determine relevant medical information. The medical data application 126 displays the relevant medical information 1202 in connection with image 1201. In addition, medical data application 126 may cause processor 150 to display a prompt 1204 asking the clinician to confirm whether the relevant medical information 1202 matches the medical information within image 1201.

Figure 13:
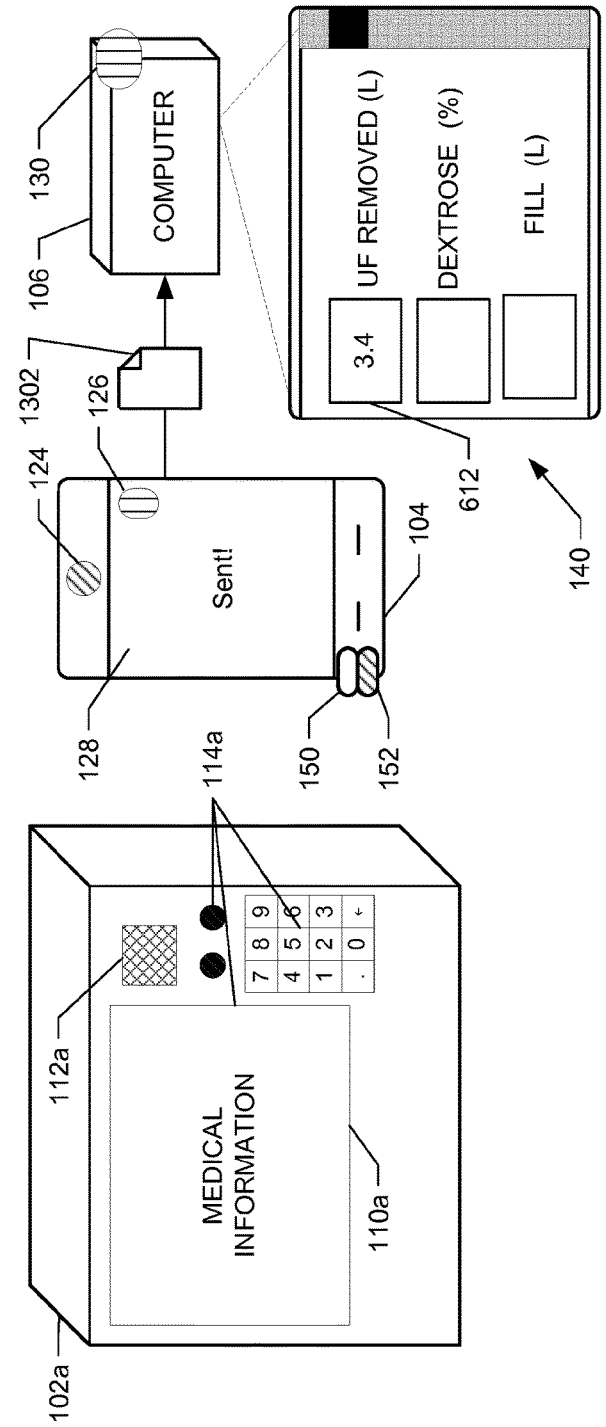

FIG. 13 shows the medical data application 126 causing processor 150 to transmit a message 1302 that includes the relevant medical information 1202. The example message 1304 may also identify the data field 612 of the patient medical template 140 to which the relevant medical information is to be stored. Alternatively, message 1302 may include label text associated with the relevant medical information, such as "UF Vol." and/or an indication of which data fields of the device data template correspond to the relevant medical information. In other examples, medical data application 126 may cause processor 150 to determine the data field of the template using, for example, a lookup table that correlates the device data fields of data template 700 to data fields of patient medical template 140. The medical data application 126 may cause processor 150 to transmit message 1302 after receiving a confirmation from the clinician (e.g., selection of the prompt 1204) indicating that relevant medical information 1202 is correct.

The template application 130 of computer 106 receives the message 1304 and locates data field 612. In some examples, template application 130 locates data field 612 using a lookup table to match the label text or identified data field of the device data template to the data field 612. Alternatively, template application 130 searches text and/or metadata associated with the data field (or information within module 658 of routine 650 of FIG. 6) to determine that data field 612 is the intended target of the data population. After identifying data field 612, example template application 130 may populate or otherwise write the relevant medical information received in message 1302 to data field 612 of patient medical template 140.

Figure 14:
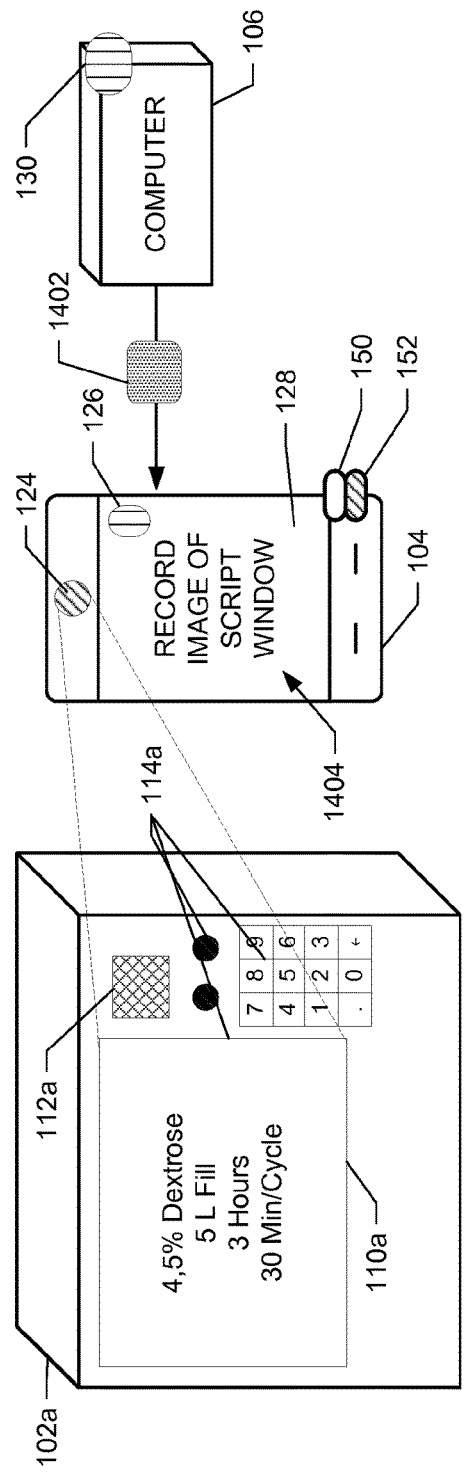

In FIG. 14, after data field 612 is populated, template application 130 may determine that medical information (e.g., % dextrose and fill level) from a prescription window of medical device 102*a* to 102*c* is needed for patient medical template 140. The template application 130 transmits a navigation/image message 1402 to the portable device 104 with information for obtaining an image of the prescription window. The message 1402 may also include a data template for the prescription window. In other instances, the data template may be transmitted separately.

The medical data application 126 causes processor 150 to display information 1304 from message 1402 on screen 128 of portable device 104, prompting the clinician to navigate to the prescription window on medical device 102*a*. In some examples, information 1304 may also include instructions for using control interface 114*a* to navigate to the window and/or an image representative of an image to be acquired. As illustrated, the prescription window, displayed in screen 110*a*, includes information about dextrose level, total fill volume, treatment time, and cycle time. The clinician may use camera 124 to record an image of the screen 110*a* showing the prescription window of medical device 102*a*.

Figure 15:
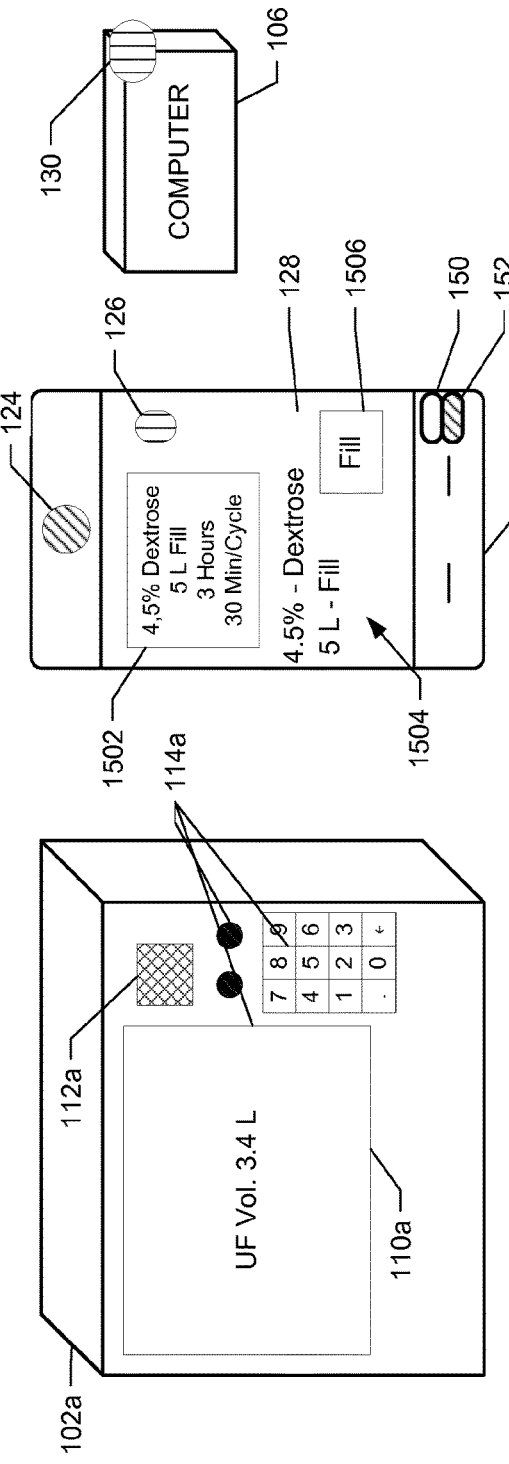

In FIG. 15, medical data application 126 causes processor 150 to extract text from the image (shown as image 1502) and uses the data template for the prescription window to identify relevant medical information 1504. The medical data application 126 causes processor 150 to display image 1502 and relevant medical information 1504 on the screen 128 of the portable device 104. The medical data application 126 also causes processor 150 to display label text (e.g., Dextrose and Fill) with the relevant medical information 1504. In addition, medical data application 126 may cause processor 150 to display a prompt 1506 requesting the clinician to confirm whether the relevant medical information 1504 matches the medical information within image 1502.

Figure 16:
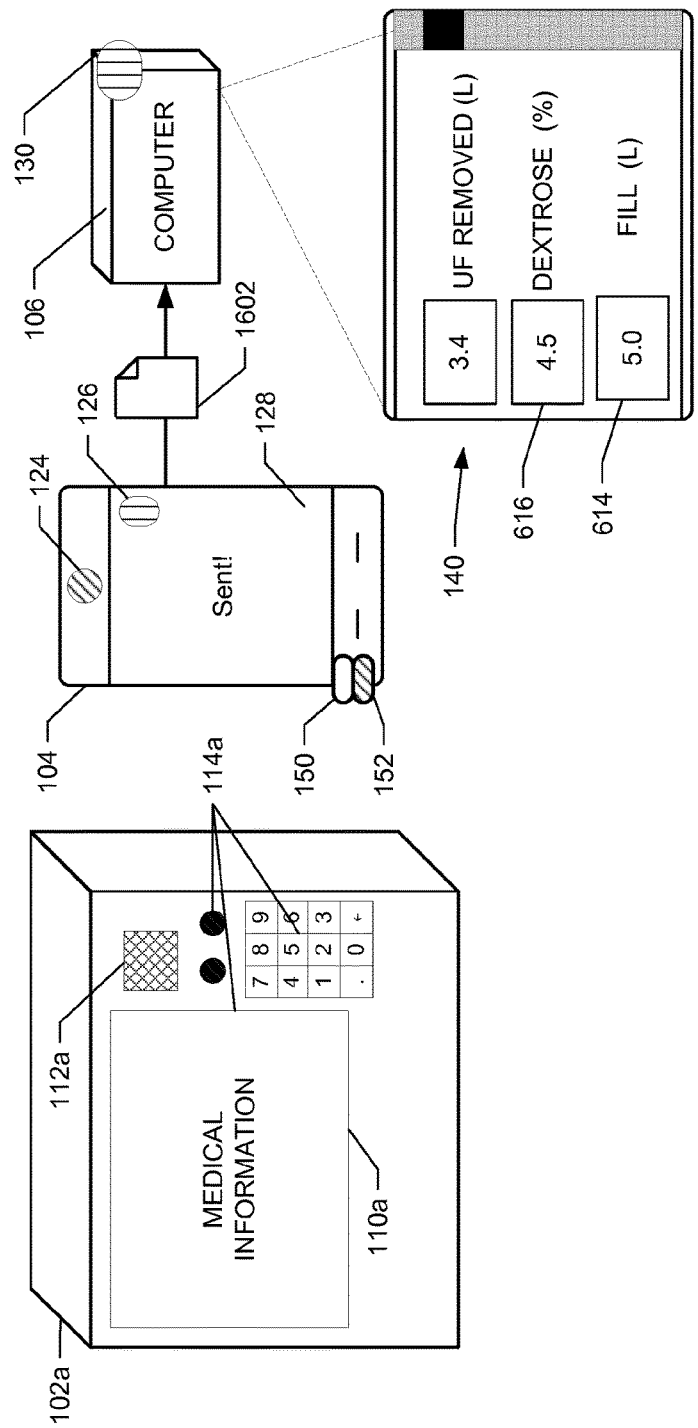

FIG. 16 shows a selection of prompt 1506 of FIG. 15 by the clinician causing relevant medical information 1504 to be transmitted in message 1602 to clinician computer 106. The example template application 130 receives message 1602 and writes the relevant medical information 1504 to appropriate data fields 614 and 616 of the patient medical template 140. As discussed above, template application 130 may determine the data fields 614 and 616 based on information in message 1602, including data labels and/or device data fields associated with the relevant medical information 1504. Alternatively, template application 130 may receive in the message 1602 information specifically identifying data fields 614 and 616. Further, as discussed above, template application 130 may format or convert relevant medical information 1504 for writing and/or check a validity of the relevant medical information 1504.

Figure 17:
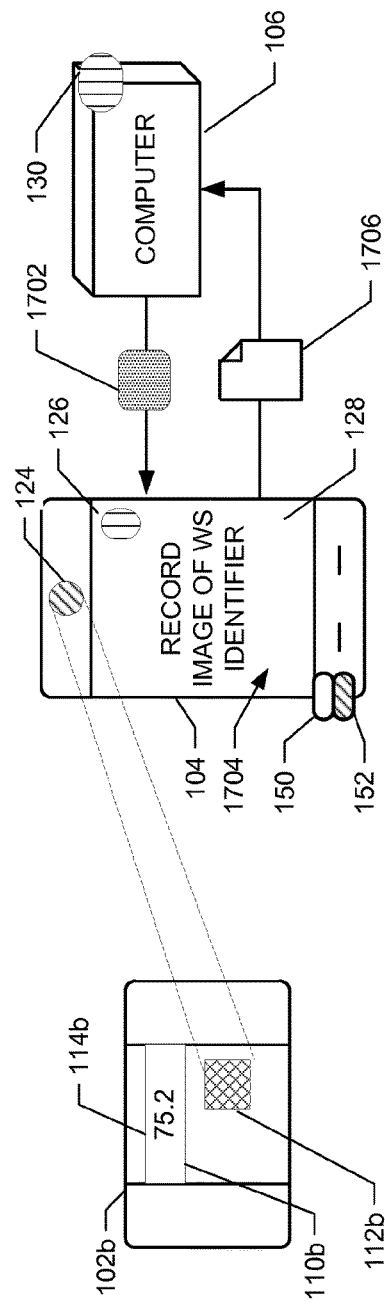

After data fields 614 and 616 are populated, template application 130 may determine that all of the data fields for the medical device 102*a* have been populated. The template application 130 executes routine 650 to determine if another medical device in the sequence exists. Specifically, template application 130 may determine that medical information from the weight scale medical device 102b is needed. Accordingly, as shown in FIG. 17, template application 130 transmits a message 1702 with information for displaying prompt 1704 asking a clinician to record an image of identifier 112b. The clinician may record an image of identifier 112b, which is analyzed by medical data application 126 to determine medical information. The medical data application 126 transmits the medical information (identifying a model or type of the medical device 102b) to computer 106 via message 1706.

In FIG. 18, template application 130 receives the medical information in message 1706 and determines a device data template for medical device 102b. In addition, template application 130 determines a camera message for recording medical information from screen 110b of the medical device 102b. The weight scale data template and message are included within one or more message 1802 transmitted to portable device 104. The example portable device 104 displays information 1804 from the message(s) 1802 prompting the clinician to record an image of screen 110b of the weight scale medical device 102b using the camera 124 of the portable device 104.

In FIG. 19, medical data application 126 extracts text from the image (shown as image 1902) and uses the weight scale data template to identify relevant medical information 1904. The medical data application 126 displays image 1902 and the relevant medical information 1904 on screen 128 of portable device 104. In addition, medical data application 126 displays a prompt 1906 requesting the clinician to confirm whether the relevant medical information 1904 matches the medical information within the image 1602.

Figure 20:
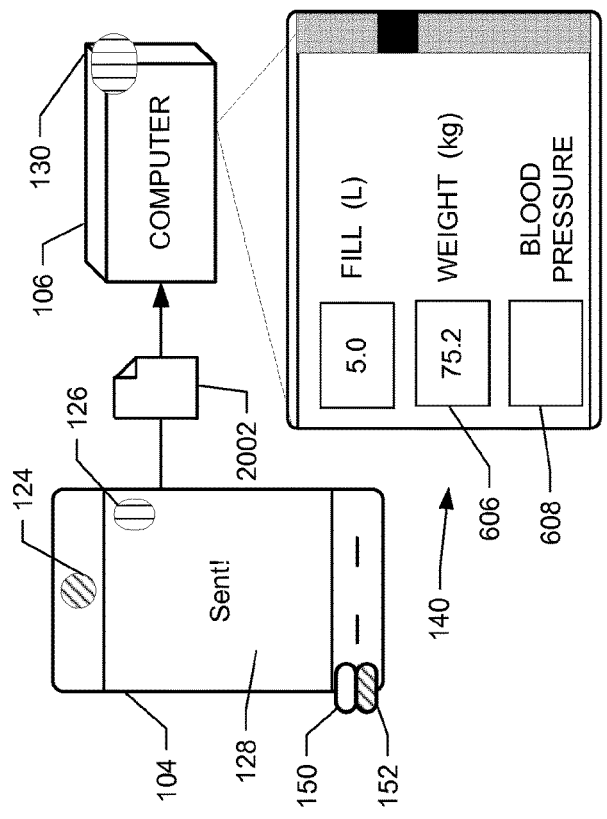

FIG. 20 shows a selection of prompt 1906 of FIG. 19 by the clinician causing the relevant medical information 1904 to be transmitted in message 2002 to clinician computer 106. The example template application 130 receives message 2002 and writes the relevant medical information 1904 to the appropriate data field 606 of patient medical template 140. The template application 130 continues until substantially all of the data fields of patient medical template 104 have been populated, including obtaining medical device information for patient 122 and/or consumable items 120 (if needed). The template application 130 may then store the populated patient medical template 140 as a patient EMR locally or at the CIS server 108.

It should be appreciated that FIGS. 10 to 20 provide only one example and that other implementations are possible. For example, FIGS. 10 to 20 show that relevant medical information is transmitted to clinician computer 106 as the data is determined. In other examples, portable device 104 may queue messages with the relevant medical information until a connection with clinician computer 106 is established or after all the data for populating the template has been obtained.

In yet other examples, portable device 104 may obtain a copy of template 140 (and possibly routine 650 as well). The portable device 104 may also contain a database of patient medical templates without having to request a copy from clinician computer 106. The portable device 104 then performs the workflow shown in FIGS. 10 to 20 locally, while not communicating with clinician computer 106 while template 140 is being populated. Instead, portable device 104, and more specifically, the medical data application 126 determines the messages that are to be displayed as well as the workflow of the corresponding steps. After template 140 is populated (or populated sufficiently as determined by the clinician), portable device 104 transmits template 140 to computer 106 for storage as an EMR.

In another embodiment, the workflow discussed above in connection with FIGS. 10 to 20 may omit camera messages that prompt a clinician to image identifiers 112. Instead, the clinician may first image an identifier 112, which then starts a sub-workflow for the medical device associated with the imaged identifier 112. For example, the template application 130 may still determine a device data template and camera messages for medical device windows based on which identifier was imaged.

Regardless of example implementation, portable device 104 operates as a keyboard such that relevant medical information extracted from the images of screens of medical devices are used as keys for populating data fields of a patient medical template.

Figure 21:
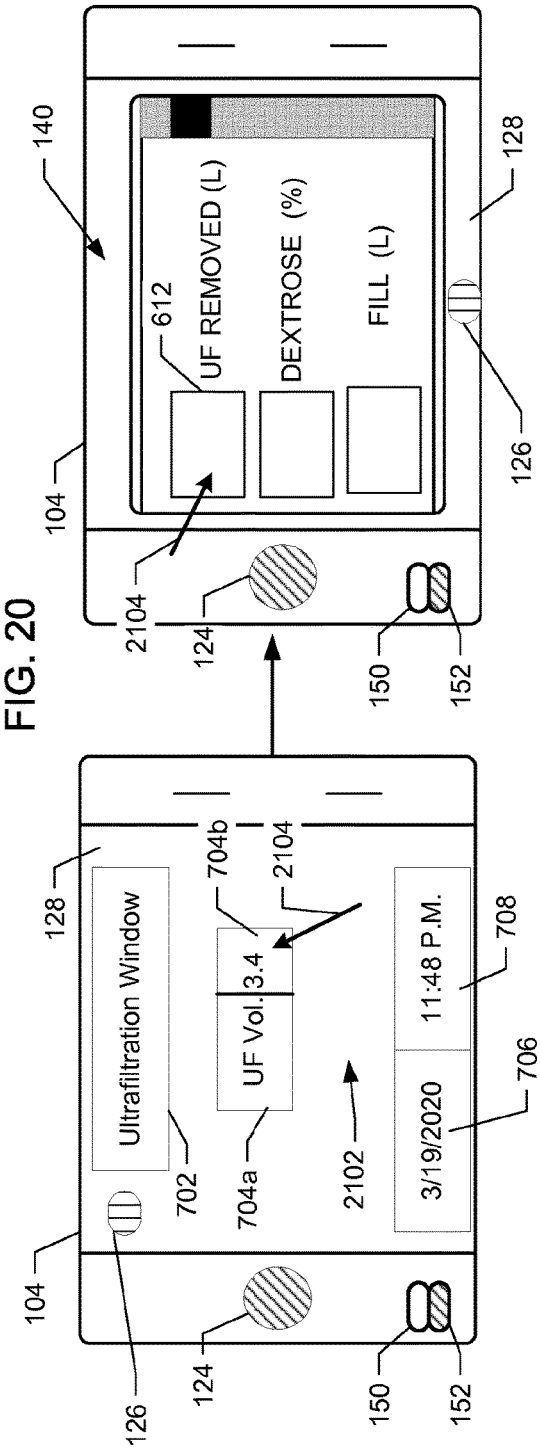
FIGS. 21 and 22 are schematic diagrams illustrating an alternative example for populating the medical device template of FIG. 6 using images recorded by the portable device of FIGS. 1, 2, and 9, according to an example embodiment of the present disclosure.
Figure 22:
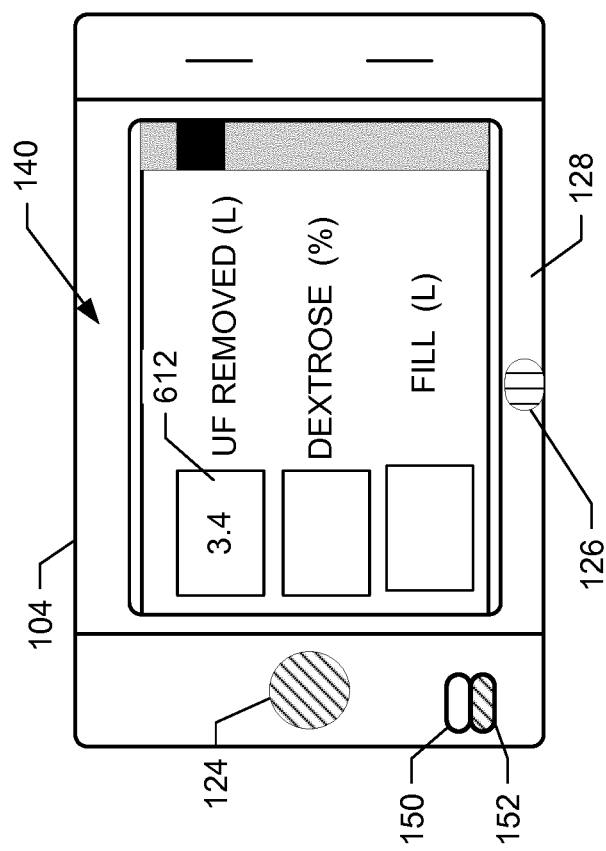

XI. Remote Population of a Patent Medical Template Workflow Alternative Example FIGS. 21 and 22 are schematic diagrams that illustrate an alternative workflow for entering medical information into a patient medical template using portable device 104, according to an example embodiment of the present disclosure. In this example, a clinician provides more direction regarding which data fields of template 140 are to be populated. FIG. 21 shows a diagram of portable device 104 having screen 128 show extracted text 2102 from an image. The extracted text 2102 is positioned based on a layout specified by, for example, data template 700 of FIG. 7. Each of the fields 702 to 708 of the template 700 includes corresponding text extracted from the image.

The medical data application 126 enables each of the data fields 702 to 708 to be selectable. A clinician selects, for example, data fields with relevant medical information for population into patient medical template 140. For example, in FIG. 21, the clinician uses cursor 2104 (e.g., their finger) to select the data field 704b with medical information of 6.4.

After selection of data field 704b, medical data application 126 causes processor 150 to display an image of patient medical template 140, as shown in FIG. 21. The image of template 140 may be an image received from clinician computer 106. Alternatively, the image of template 140 may graphically represent template 140 (or a copy of the template 140 provided by clinician computer 106) at portable device 104. Each of the data fields of template 140 are selectable. A clinician uses cursor 2104 to select which data field 612 of patient medical template 140 is to be populated. Selection of the data field 612 instructs the medical data application 126 to store the medical information from the data field 704b to that data field 612.

As illustrated in FIG. 22, medical data application 126 may write or otherwise populate the data field 612 of patient medical template 140 with the medical information of "3.4". The medical data application 126 causes processor 150 to perform a similar workflow for other images recorded by portable device 104 until the clinician is finished populating template 140. In some instances, medical data application 126 may arrange the images with the extracted text as separate windows or tabs that a clinician may navigate through to sequentially populate the template. Accordingly, portable device 104 operates as a keyboard such that relevant medical information extracted from images of screens of medical devices 102 are used as keys for populating data fields of a patient medical template 140.

Flowcharts of Example Processes to Populate a Patent Medical Template

Figure 23:
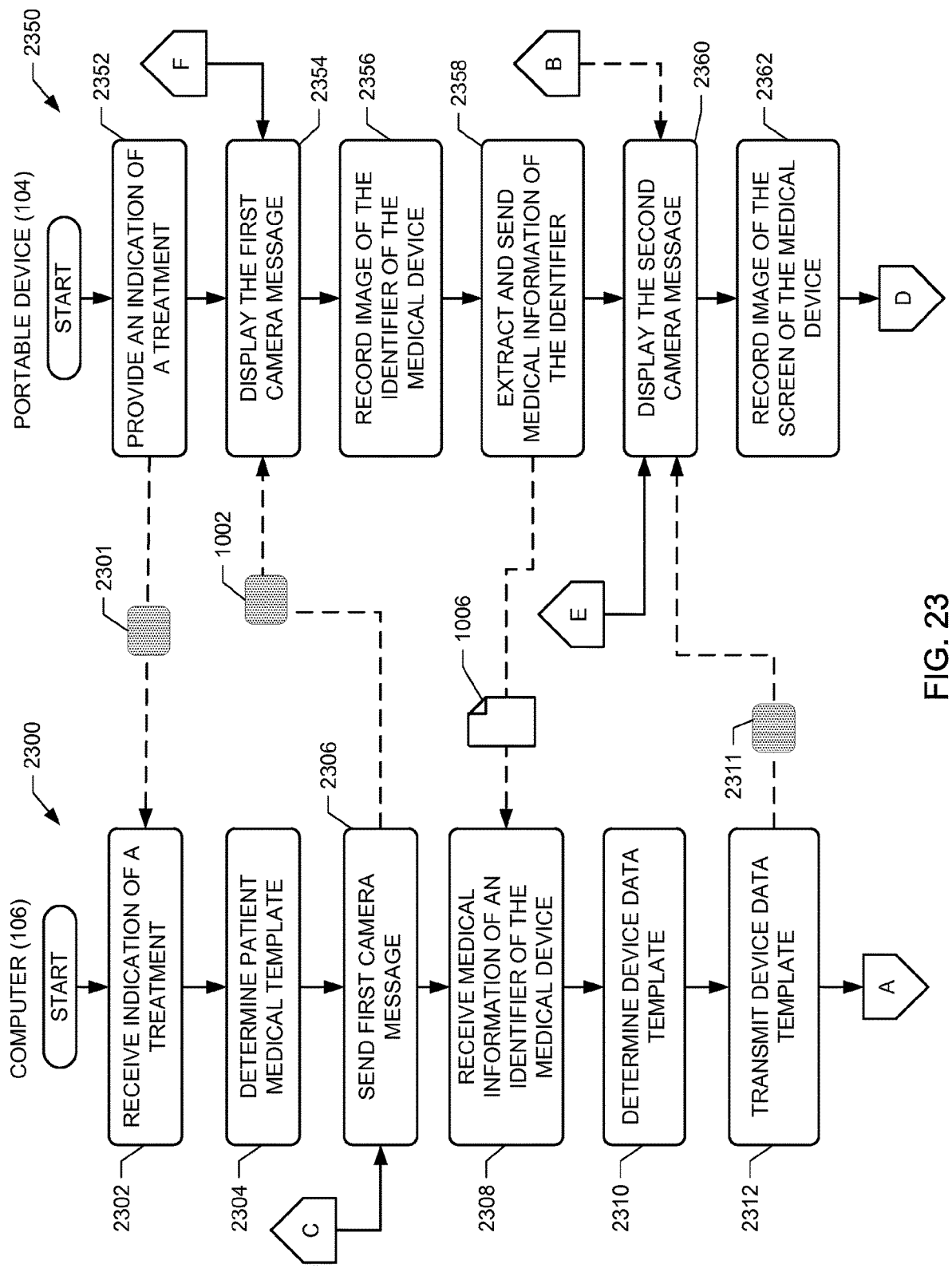
FIGS. 23 and 24 are schematic flow diagrams illustrating procedures to populate the medical device template of FIG. 6 using images recorded by the portable device of FIGS. 1, 2, and 9, according to an example embodiment of the present disclosure.
Figure 24:
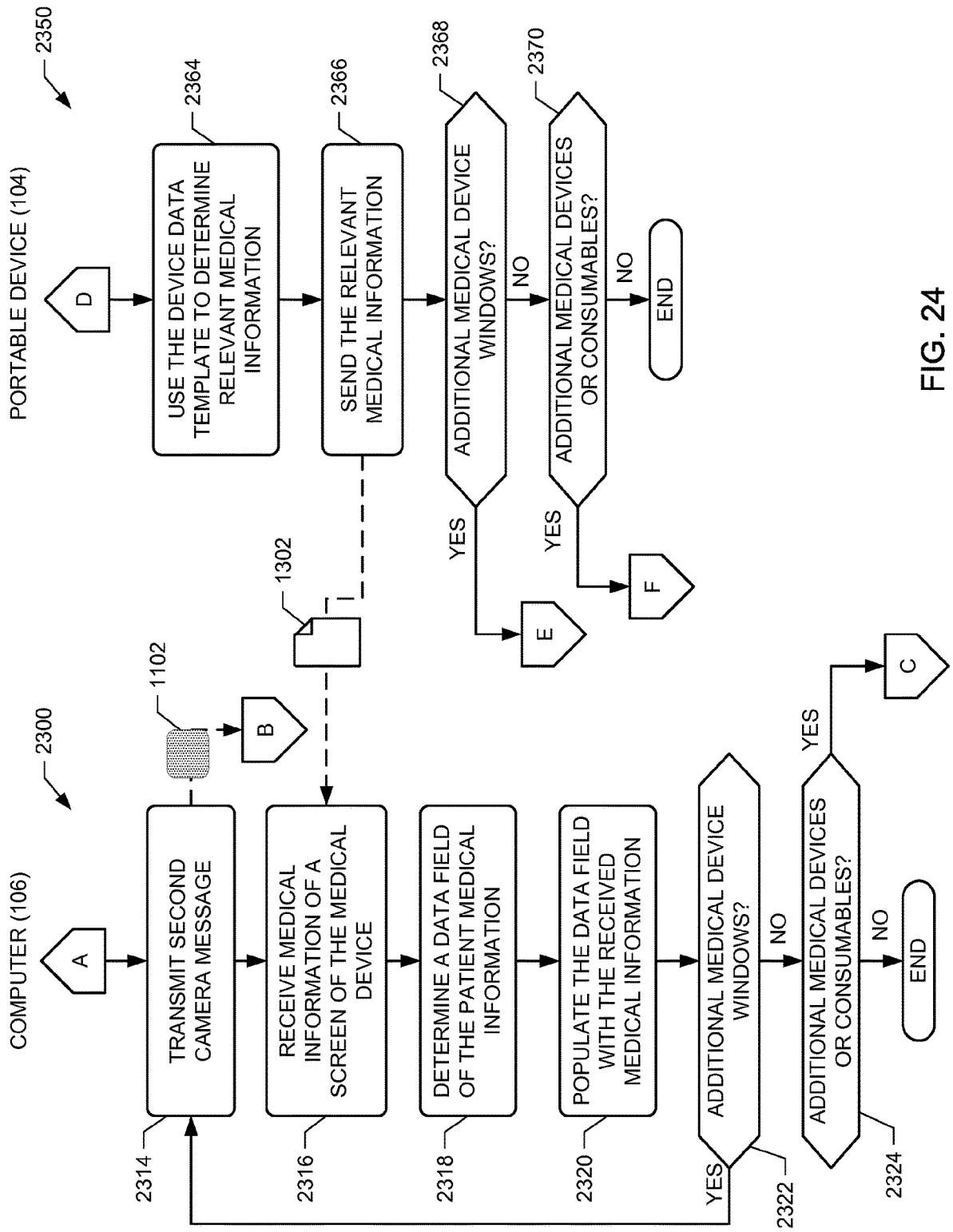

FIGS. 23 and 24 are flow diagrams of example procedures 2300 and 2350 to populate medical device template 140 of FIG. 6 using images recorded by portable device 104 of FIGS. 1, 2, and 9, according to an example embodiment of the present disclosure. Although procedures 2300 and 2350 are described with reference to the flow diagram illustrated in FIGS. 23 and 24, it should be appreciated that many other methods of performing the steps associated with the procedures 2300 and 2350 may be used. For example, the order of many of the blocks may be changed, certain blocks may be combined with other blocks, and many of the blocks described may be optional. For example, the order of the blocks may be modified if a persistent connection does not exist between computer 106 and portable device 104 of FIGS. 1, 2, 8, and 9. Instead, for example, portable device 104 may first acquire and queue substantially all relevant medical information for a patient medical template until a connection with computer 106 is available (or by design). This may include portable device 104 determining a patient medical template, device data template, and/or prompts for an operator. Further, the actions described in procedures 2300 and 2350 may be performed among multiple devices including, for example portable device 104 and clinician or CIS computer 106.

The example procedure 2300 begins in FIG. 23 when computer 106 of FIGS. 1, 2, and 9 receives a message 2301 from portable device 104 (block 2302). The message 2301 is indicative of a treatment to be performed on a patient. Computer 106 then determines a patient medical template (e.g., the patient medical template 140 of FIG. 6) based on the treatment type specified in message 2301 (block 2304). Additionally or alternatively, computer 106 may establish a session with portable device 104 for completing patent medical template 140 based on the specified treatment. In instances where computer 106 only provides for the completion of one type of template (e.g., a template for a renal failure therapy), message 2301 may simply indicate a request to start populating a blank template. In response, computer 106 creates a copy of the patient medical template for population.

After providing a patient medical template for population, computer 106 determines at least one medical device 102 from which medical information is needed and accordingly transmits a first camera message 1002 to portable device 104 (block 2306). As discussed above in conjunction with FIG. 10, first camera message 1002 includes instructions indicating that an image is to be recorded of an identifier 112 of a medical device 102. Some time later, computer 106 receives a message 1006 that includes medical information indicative of a type of medical device 102 (e.g., medical information from an identifier 112) (block 2308). The computer 106 then determines a device data template (e.g., device data template 700 of FIG. 7) based on information included within the message 1006 (block 2310). For example, upon determining that message 1006 identifies a renal failure therapy machine medical device 102a (type and/or model), computer 106 determines or locates a device data template for the renal failure therapy medical device 102a. The computer 106 transmits the device data template to portable device 104 via message 2311 (block 2312).

Example procedure 2300 continues in FIG. 24 where computer 106 transmits a second camera message 1102 to portable device 104 (block 2314). The second camera message 1102 may be determined based on a type of medical device specified by the message 1006. Further second camera message 1102 may include information for displaying a certain window (or otherwise identified relevant medical information) on a medical device 102 for recording an image. Some time later computer 106 receives a message 1002 that includes relevant medical information for populating certain fields of a patient medical template (block 2316). In some embodiments, the message 1002 may identify the data fields of the template and/or include label information to enable computer 106 to determine the data fields. The example computer 106 determines or otherwise identifies the data fields on the patient medical template that correspond to the relevant medical information contained in message 1002 (block 2318). Computer 106 next populates the determined and/or identified data fields of the template with the relevant received medical information (block 2320).

After populating the relevant data fields, example computer 106 determines if additional relevant medical information is needed from medical device 102 associated with the received relevant medical information (decision block 2322). For example, computer 106 may determine that the current medical device 102 may include additional windows or operating displays from which relevant medical information is still needed. If additional medical information is needed, example computer 106 returns to block 2314 and transmits a camera message 1102 for another window for which relevant medical information is needed. However, if no additional medical information is needed for the current medical device 102, computer 106 determines if medical information is needed from other medical devices 102 (or consumable item 120) (decision block 2324). If additional medical information is needed, computer 106 returns to block 2306 and transmits a camera message 1002 identifying another medical device 102 for imaging. If no additional medical information is needed for completion of the patient medical template 140, example computer 106 stores the completed patient medical template 140 to a database or transmits the template to CIS server 108 as a patient's EMR and procedure 2300 ends.

The example procedure 2350 begins on FIG. 23 by portable device 104 transmitting a message 2301 that is indicative of a treatment to be performed on a patient (2052). The example portable device 104 may also open a session and/or secure network connection with computer 106 for completing a patient medical template associated with the specified treatment. Portable device 104 receives a camera message 1002 from computer 106. Information from the message 1002 is used by portable device 104 to display a prompt to an operator (block 2354). The prompt may specify, for example, that an identifier 112 of medical device 102 is to be imaged. Portable device 104 then records an image of identifier 112 of the medical device 102 (block 2356) based on input from the operator. In some embodiments, the operator may enter text specifying a medical device type/model or select from a drop-down menu if an identifier is not available.

After receiving an image of identifier 112, portable device 104 extracts or otherwise determines medical information encoded in the identifier (block 2358). Portable device 104 sends the extracted medical information in a message 1006 to computer 106. Afterwards, portable device 104 receives a camera message 1102 from computer 106 with information for displaying a prompt to an operator for recording an image of screen 110 (or other specified area) of medical device 102 (block 2360). Portable device 104 may also receive a message 2311 with a device data template associated with the medical device to be imaged. The portable device 104 accordingly display a prompt to the operator with information identifying information needed for imaging from a medical device. Responsive to the prompt, the operator uses portable device 104 to record an image of screen 110 (or other specified area) of medical device 102 (block 2362).

In FIG. 24, example procedure 2350 continues by portable device 104 extracting text from the image and applying the device data template to the extracted text to determine relevant medical information (block 2364). In some examples, the operator may modify or specify the relevant medical information. Further, in some examples, portable device 104 determines data field(s) of the patient medical template for the relevant medical information or labels (e.g., metadata) that describe the relevant medical derive data. Portable device 104 then transmits a message 1302 that includes the relevant medical information (block 2366). The message 1302 may also include information that identifies data fields of the template and/or data labels used by computer 106 for determining data fields.

Example portable device 104 next determines if additional relevant medical information is needed from medical device 102 associated with the extracted relevant medical information (decision block 2368). The determination may include, for example, checking to see if additional camera messages related to the current medical device 102 are received from computer 106 (block 2360). If additional medical information is needed, example portable device 104 returns to block 2360 and processes a camera message 1102 for another window for which relevant medical information is needed. However, if no additional medical information is needed for the current medical device 102, portable device 104 determines if medical information is needed from other medical devices 102 (or consumable item 120) (decision block 2370). If additional medical information is needed, portable device 104 returns to block 2354 and processes a camera message 1002 identifying another medical device 102 for imaging. If no additional medical information is needed for adequate completion of the patient medical template, example portable device 104 ends the session, thereby ending the procedure 2350.

CONCLUSION

It will be appreciated that each of the disclosed methods and procedures described herein may be implemented using one or more computer program or component. These components may be provided as a series of computer instructions on any computer-readable medium, including RAM, ROM, flash memory, magnetic or optical disks, optical memory, or other storage media. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A portable device for transmitting medical data to a clinician computer, the portable device comprising:
   a camera configured to record images;
   a memory storing the recorded images;
   a display interface for displaying the images; and
   a processor configured to execute machine-readable instructions, which when executed, cause the processor to:
   (i) determine a type of a medical device that is to be imaged,
   (ii) use the determined type of the medical device to determine whether a message is to be displayed, and if so, display a navigation message via the display interface prompting an operator to navigate to a specified window that is displayed by a screen of the medical device,
   (iii) instruct the camera to record at least one image,
   (iv) extract medical data from the at least one image using an optical character recognition routine,
   (v) establish a connection with the clinician computer such that the portable device is recognized by the clinician computer as a keyboard, and
   (vi) transmit at least some of the extracted medical data to the clinician computer as a keyboard input to the clinician computer,
   wherein the processor is configured to enable the at least some of the extracted medical data from the at least one image to be transmitted as the keyboard input to the clinician computer by enabling selection, via the display interface, of the at least some of the extracted medical data for transmission.

2. The device of claim 1, wherein the connection includes at least one of a Bluetooth® connection or a Zigbee® connection.

3. The device of claim 1, wherein the processor is configured to specify itself as being of at least one of (i) a universal serial bus ("USB") human interface device ("HID") class or (ii) a Bluetooth® HID profile to the clinician computer such that the portable device is recognized as the keyboard input by the clinician computer.

4. The device of claim 3, wherein the processor is configured to transmit at least one device driver file including USB HID class information or Bluetooth® HID information to the clinician computer to establish the connection.

5. The device of claim 1, wherein the processor is configured to establish the connection with the clinician computer by causing the clinician computer to operate a device driver for communication with the processor.

6. The device of claim 1, wherein the processor is configured to:
   before (i), display a camera message via the display interface prompting the operator to use the camera to record a medical device image;
   extract medical device data from the medical device image using the optical character recognition routine; and
   determine, as part of the extracted medical device data, the type of the medical device from the medical device image.

7. The device of claim 1, wherein the processor is configured to enable the operator to select a portion of the extracted medical data for transmission to the clinician computer based on the determined type of the medical device.

8. The device of claim 1, wherein the memory stores at least one data template for processing the at least one image, the data template configured to organize the extracted medical data.

9. The device of claim 1, wherein the processor is configured to cause the display interface to display a camera message that prompts the operator to use the camera to record, in the at least one image, an identifier of the medical device, the identifier including at least one of a quick-response ("QR") code, a barcode, a serial number, or a hardware number located on a housing of the medical device or the screen of the medical device.

10. The device of claim 9, wherein the processor analyzes the identifier by at least one of decoding a pattern within the recorded image or performing optical character recognition on the identifier.

11. The device of claim 1, wherein the processor is configured to display a verification message via the display interface prompting the operator to confirm that the extracted medical data matches data in the at least one image.

12. The device of claim 1, wherein the at least one image is of a consumable item, the extracted medical data being consumable data, and wherein the processor is configured to transmit the consumable data to the clinician computer as the keyboard input.

13. The device of claim 12, wherein the consumable data includes data concerning at least one of a filter, a blood line set, a dialysis fluid concentrate container, a blood anticoagulant container, a medication container, a peritoneal dialysis cassette, a sorbent cartridge, or a drug infusion line set.

14. The device of claim 12, wherein the processor is further configured to prompt the operator to record the at least one image of the consumable item.

15. The device of claim 1, wherein the at least one image is of a medical device parameter setting, a medical device reading, or a patient reading, the extracted medical data being medical device parameter setting data, medical device reading data, or patient reading data, and wherein the processor is configured to transmit the medical device parameter setting data, the medical device reading data, or the patient reading data to the clinician computer as the keyboard input.

16. The device of claim 15, wherein the medical device parameter setting, the medical device reading, or the patient reading is recorded from the medical device including at least a renal failure therapy machine, an infusion pump, an oxygen sensor, a respiratory monitor, a glucose meter, a blood pressure monitor, an electrocardiography ("ECG") monitor, a weight scale, or a heart rate monitor.

17. The device of claim 15, wherein the processor is further configured to prompt the operator to record the at least one image of the medical device parameter setting, the medical device reading, or the patient reading.

18. The device of claim 1, wherein the processor is further configured to assign a patient identifier to the extracted medical data, and wherein the patient identifier includes at least one of a quick-response ("QR") code, a text string, a barcode, a name, or a patient identifier located on a patient wristband.

19. An application for operation on a portable device, the device configured to transmit medical data to a clinician computer, the application comprising non-transitory machine-readable instructions, which when executed, cause the application to:
   operate with a processor of the portable device to determine a type of a medical device that is to be imaged;
   operate with the processor of the portable device to use the determined type of the medical device to determine whether a message is to be displayed, and if so, display a navigation message via a display interface of the portable device prompting an operator to navigate to a specified window that is displayed by a screen of the medical device;
   operate with the processor of the portable device to extract medical data from at least one image received from a camera of the portable device and displayed on the display interface of the portable device;
   operate with the processor and the display interface of the portable device to enable at least some of the extracted medical data to be selected for transmission;
   operate with the processor of the portable device to establish a connection with the clinician computer such that the portable device is recognized by the clinician computer as a keyboard; and
   operate with the processor of the portable device to transmit the at least some of the extracted medical data to the clinician computer as a keyboard input to the clinician computer.

20. The application of claim 19, which includes additional machine-readable instructions, which when executed, cause the application to operate with the processor to display a message via the display interface of the portable device prompting the operator to record the at least one image.

21. The application of claim 19, which includes additional machine-readable instructions, which when executed, cause the application to:
   receive a selection, via the display interface of the portable device, indicative of a portion of the extracted medical data; and
   transmit the selected portion of the extracted medical data to the clinician computer as the keyboard input to the clinician computer.

22. A method for transmitting medical data to a clinician computer, the method comprising:
   receiving, in an application operating on a portable device, an indication of a type of a medical device that is to be imaged;
   using, in the application operating on the portable device, the determined type of the medical device to determine whether a message is to be displayed, and if so, displaying a navigation message via a display interface of the portable device prompting an operator to navigate to a specified window that is displayed by a screen of the medical device;
   receiving, in the application operating on the portable device, at least one image recorded by a camera of the portable device;
   displaying the at least one image on the display interface of the portable device;
   extracting, via a processor of the portable device, medical data from the at least one image;
   enabling, via the processor and the display interface of the portable device, at least some of the extracted medical data to be selected for transmission;
   establishing, using the application operating on the portable device, a connection with the clinician computer such that the portable device is recognized by the clinician computer as a keyboard; and
   transmitting, using the application operating on the portable device, the at least some of the extracted medical data to the clinician computer as a keyboard input to the clinician computer.

23. The method of claim 22, wherein establishing the connection with the clinician computer includes causing the portable device to emulate a keyboard with respect to a serial interface of the clinician computer.

24. The method of claim 22, further comprising:
   extracting, via the application, the extracted medical data using a data template that organizes the at least one image; and
   transmitting, using the application operating on the portable device, the extracted medical data to the clinician computer as the keyboard input to the clinician computer.

25. The method of claim 24, wherein the data template is recorded by the camera on the portable device of a screen of the clinician computer.

26. The method of claim 22, further comprising:
   receiving a selection from the display interface indicative of (i) one of the at least one image, or (ii) a portion of the extracted medical data from the at least one image; and
   transmitting (i) the extracted medical data from the selected image, or (ii) the selected portion of the extracted medical data to the clinician computer as the keyboard input to the clinician computer.

27. The method of claim 22, further comprising:
   causing, using the application operating on the portable device, a speaker of the portable device to provide an announcement of at least a portion of the extracted medical data from the selected image; and
   receiving, using the application operating on the portable device, a validation indication that the announced extracted medical data is to be transmitted as the keyboard input.

28. The method of claim 22, further comprising displaying a message prompting the operator to use the camera of the portable device to record the at least one image.

* * * * *